(12) United States Patent
Reiter et al.

(10) Patent No.: US 9,946,711 B2
(45) Date of Patent: Apr. 17, 2018

(54) TEXT GENERATION FROM CORRELATED ALERTS

(71) Applicant: Arria Data2Text Limited, Aberdeen (GB)

(72) Inventors: Ehud B. Reiter, Aberdeen (GB); Alasdair Logan, Aberdeen (GB); Lucia Ortega Alvarez, Aberdeen (GB); Edward Apeh, Aberdeen (GB); Bracha Libman, Aberdeen (GB); William Bradshaw, Aberdeen (GB)

(73) Assignee: ARRIA DATA2TEXT LIMITED, Aberdeen (GB)

( * ) Notice: Subject to any disclaimer, the term of this patent is extended or adjusted under 35 U.S.C. 154(b) by 0 days.

(21) Appl. No.: 14/914,461

(22) PCT Filed: Aug. 29, 2013

(86) PCT No.: PCT/IB2013/058131
§ 371 (c)(1),
(2) Date: Feb. 25, 2016

(87) PCT Pub. No.: WO2015/028844
PCT Pub. Date: Mar. 5, 2015

(65) Prior Publication Data
US 2016/0217133 A1 Jul. 28, 2016

(51) Int. Cl.
*G06F 17/28* (2006.01)
*G08B 5/22* (2006.01)
(Continued)

(52) U.S. Cl.
CPC ........... *G06F 17/2881* (2013.01); *G08B 5/22* (2013.01); *A61B 5/024* (2013.01); *A61B 5/0816* (2013.01)

(58) Field of Classification Search
CPC ..... G06F 17/30654; G06F 17/28; G10L 15/18
See application file for complete search history.

(56) References Cited

U.S. PATENT DOCUMENTS 5,181,250 A 1/1993 Morgan et al.
5,237,502 A 8/1993 White et al.
(Continued)

FOREIGN PATENT DOCUMENTS

AU 2011247830 B2 12/2011
AU 2011253627 B2 12/2011
(Continued)

OTHER PUBLICATIONS

Yu, Jin, et al. "SumTime-turbine: a knowledge-based system to communicate gas turbine time-series data." International Conference on Industrial, Engineering and Other Applications of Applied Intelligent Systems. Springer Berlin Heidelberg, 2003.*
(Continued)

*Primary Examiner* — Jialong He
(74) *Attorney, Agent, or Firm* — Alston & Bird LLP

(57) ABSTRACT

Methods, apparatuses, and computer program products are described herein that are configured to generate an operator text in response to an alarm that is either received from an alarm or alert system or that is self-generated based on an analysis of one or more data feeds. The method of an example embodiment may include determining whether an operator text is to be generated in response to a received alert condition by performing data analysis operations comprising: analyzing, using a processor, a primary data feed and at least one confirmatory data feed to identify one or more features; and determining based on the detection of a feature in the primary data feed or the at least one confirmatory data feed satisfies at least one predetermined constraint. The method may further include generating an output text that is displayable in a user interface that describes at least a
(Continued)

diagnosis for the feature that satisfied that at least one predetermined constraint.

21 Claims, 8 Drawing Sheets

(51) Int. Cl.
*A61B 5/024* (2006.01)
*A61B 5/08* (2006.01)

(56) References Cited

U.S. PATENT DOCUMENTS

| | | |
|---|---|---|
| 5,311,429 A | 5/1994 | Tominaga |
| 5,321,608 A | 6/1994 | Namba et al. |
| 5,794,177 A | 8/1998 | Carus et al. |
| 5,802,488 A | 9/1998 | Edatsune |
| 6,023,669 A | 2/2000 | Suda et al. |
| 6,078,914 A | 6/2000 | Redfern |
| 6,138,087 A | 10/2000 | Budzinski |
| 6,466,899 B1 | 10/2002 | Yano et al. |
| 6,665,640 B1 | 12/2003 | Bennett et al. |
| 6,947,885 B2 | 9/2005 | Bangalore et al. |
| 7,043,420 B2 | 5/2006 | Ratnaparkhi |
| 7,167,824 B2 | 1/2007 | Kallulli |
| 7,231,341 B2 | 6/2007 | Bangalore et al. |
| 7,305,336 B2 | 12/2007 | Polanyi et al. |
| 7,346,493 B2 | 3/2008 | Ringger et al. |
| 7,418,447 B2 | 8/2008 | Caldwell et al. |
| 7,496,621 B2 | 2/2009 | Pan et al. |
| 7,526,424 B2 | 4/2009 | Corston-Oliver et al. |
| 7,533,089 B2 | 5/2009 | Pan et al. |
| 7,562,005 B1 | 7/2009 | Bangalore et al. |
| 7,684,991 B2 | 3/2010 | Stohr et al. |
| 7,711,581 B2 | 5/2010 | Hood et al. |
| 7,783,486 B2 | 8/2010 | Rosser et al. |
| 7,809,552 B2 | 10/2010 | Pan et al. |
| 7,849,048 B2 | 12/2010 | Langseth et al. |
| 7,849,049 B2 | 12/2010 | Langseth et al. |
| 7,856,390 B2 | 12/2010 | Schiller |
| 7,873,509 B1 | 1/2011 | Budzinski |
| 7,921,091 B2 | 4/2011 | Cox et al. |
| 7,930,169 B2 | 4/2011 | Billerey-Mosier |
| 7,933,774 B1 | 4/2011 | Begeja et al. |
| 7,966,172 B2 | 6/2011 | Ruiz et al. |
| 7,970,601 B2 | 6/2011 | Burmester et al. |
| 7,979,267 B2 | 7/2011 | Ruiz et al. |
| 8,019,610 B2 | 9/2011 | Walker et al. |
| 8,024,331 B2 | 9/2011 | Calistri-Yeh et al. |
| 8,037,000 B2 | 10/2011 | Delmonico et al. |
| 8,082,144 B1 | 12/2011 | Brown et al. |
| 8,090,727 B2 | 1/2012 | Lachtarnik et al. |
| 8,150,676 B1 | 4/2012 | Kaeser |
| 8,175,873 B2 | 5/2012 | Di Fabbrizio et al. |
| 8,180,647 B2 | 5/2012 | Walker et al. |
| 8,180,758 B2 | 5/2012 | Cornali |
| 8,229,937 B2 | 7/2012 | Kiefer et al. |
| 8,355,903 B1 | 1/2013 | Birnbaum et al. |
| 8,374,848 B1 | 2/2013 | Birnbaum et al. |
| 8,425,325 B2 | 4/2013 | Hope |
| 8,473,911 B1 | 6/2013 | Baxter |
| 8,494,944 B2 | 7/2013 | Schiller |
| 8,515,733 B2 | 8/2013 | Jansen |
| 8,548,814 B2 | 10/2013 | Manuel-Devadoss |
| 8,548,915 B2 | 10/2013 | Antebi et al. |
| 8,561,014 B2 | 10/2013 | Mengusoglu et al. |
| 8,566,090 B2 | 10/2013 | Di Fabbrizio et al. |
| 8,589,148 B2 | 11/2013 | Atallah et al. |
| 8,589,172 B2 | 11/2013 | Alonso et al. |
| 8,620,669 B2 | 12/2013 | Walker et al. |
| 8,630,844 B1 | 1/2014 | Nichols et al. |
| 8,655,889 B2 | 2/2014 | Hua et al. |
| 8,676,691 B2 | 3/2014 | Schiller |
| 8,688,434 B1 | 4/2014 | Birnbaum et al. |
| 8,700,396 B1 | 4/2014 | Mengibar et al. |
| 8,738,384 B1 | 5/2014 | Bansal et al. |
| 8,738,558 B2 | 5/2014 | Antebi et al. |
| 8,762,133 B2 | 6/2014 | Reiter |
| 8,762,134 B2 | 6/2014 | Reiter |
| 8,775,161 B1 | 7/2014 | Nichols et al. |
| 8,825,533 B2 | 9/2014 | Basson et al. |
| 8,843,363 B2 | 9/2014 | Birnbaum et al. |
| 8,849,670 B2 | 9/2014 | Di Cristo et al. |
| 8,886,520 B1 | 11/2014 | Nichols et al. |
| 8,892,417 B1 | 11/2014 | Nichols et al. |
| 8,892,419 B2 | 11/2014 | Lundberg et al. |
| 8,898,063 B1 | 11/2014 | Sykes et al. |
| 8,903,711 B2 | 12/2014 | Lundberg et al. |
| 8,903,718 B2 | 12/2014 | Akuwudike |
| 8,909,595 B2 | 12/2014 | Gandy et al. |
| 8,914,452 B2 | 12/2014 | Boston et al. |
| 8,924,330 B2 | 12/2014 | Antebi et al. |
| 8,930,305 B2 | 1/2015 | Namburu et al. |
| 8,977,953 B1 | 3/2015 | Pierre et al. |
| 9,002,695 B2 | 4/2015 | Watanabe et al. |
| 9,002,869 B2 | 4/2015 | Riezler et al. |
| 9,015,730 B1 | 4/2015 | Allen et al. |
| 9,028,260 B2 | 5/2015 | Nanjiani et al. |
| 9,092,276 B2 | 7/2015 | Allen et al. |
| 9,104,720 B2 | 8/2015 | Rakshit et al. |
| 9,110,882 B2 | 8/2015 | Overell et al. |
| 9,110,977 B1 | 8/2015 | Pierre et al. |
| 9,111,534 B1 | 8/2015 | Sylvester et al. |
| 9,135,244 B2 | 9/2015 | Reiter |
| 9,135,662 B2 | 9/2015 | Evenhouse et al. |
| 9,146,904 B2 | 9/2015 | Allen |
| 9,164,982 B1 | 10/2015 | Kaeser |
| 9,190,054 B1 | 11/2015 | Riley et al. |
| 9,208,147 B1 | 12/2015 | Nichols et al. |
| 9,229,927 B2 | 1/2016 | Wolfram et al. |
| 9,240,197 B2 | 1/2016 | Begeja et al. |
| 9,244,894 B1 | 1/2016 | Dale et al. |
| 9,251,134 B2 | 2/2016 | Birnbaum et al. |
| 9,251,143 B2 | 2/2016 | Bird et al. |
| 9,263,039 B2 | 2/2016 | Di Cristo et al. |
| 9,268,770 B1 | 2/2016 | Kursun |
| 9,323,743 B2 | 4/2016 | Reiter |
| 2003/0212545 A1 | 11/2003 | Kallulli |
| 2004/0246120 A1 | 12/2004 | Benner et al. |
| 2005/0015681 A1* | 1/2005 | Strole ................ G05B 23/0221 714/47.1 |
| 2005/0228635 A1 | 10/2005 | Araki et al. |
| 2006/0074597 A1* | 4/2006 | Raphael .............. G06F 11/0793 702/183 |
| 2006/0259293 A1 | 11/2006 | Orwant |
| 2007/0078655 A1 | 4/2007 | Semkow et al. |
| 2007/0106628 A1 | 5/2007 | Adjali et al. |
| 2007/0143099 A1 | 6/2007 | Balchandran et al. |
| 2007/0287929 A1* | 12/2007 | Goedje .............. A61B 5/02028 600/526 |
| 2008/0221865 A1 | 9/2008 | Wellmann |
| 2008/0221870 A1 | 9/2008 | Attardi et al. |
| 2008/0312954 A1 | 12/2008 | Ullrich et al. |
| 2009/0089100 A1 | 4/2009 | Nenov et al. |
| 2009/0089126 A1 | 4/2009 | Odubiyi |
| 2009/0111486 A1 | 4/2009 | Burstrom |
| 2009/0156229 A1 | 6/2009 | Hein et al. |
| 2009/0198496 A1 | 8/2009 | Denecke |
| 2010/0146491 A1 | 6/2010 | Hirano et al. |
| 2010/0153095 A1 | 6/2010 | Yang et al. |
| 2010/0174545 A1 | 7/2010 | Otani |
| 2010/0191658 A1 | 7/2010 | Kannan et al. |
| 2010/0332235 A1 | 12/2010 | David |
| 2011/0010164 A1 | 1/2011 | Williams |
| 2011/0160986 A1 | 6/2011 | Wu et al. |
| 2011/0179006 A1 | 7/2011 | Cox et al. |
| 2011/0218822 A1 | 9/2011 | Buisman et al. |
| 2011/0257839 A1 | 10/2011 | Mukherjee |
| 2012/0078888 A1 | 3/2012 | Brown et al. |
| 2012/0136649 A1 | 5/2012 | Freising et al. |
| 2012/0173475 A1 | 7/2012 | Ash et al. |
| 2012/0290289 A1 | 11/2012 | Manera et al. |
| 2012/0310990 A1 | 12/2012 | Viegas et al. |
| 2013/0030810 A1 | 1/2013 | Kopparapu et al. |

(56) References Cited

U.S. PATENT DOCUMENTS

| | | |
|---|---|---|
| 2013/0066873 A1 | 3/2013 | Salvetti et al. |
| 2013/0151238 A1 | 6/2013 | Beaurpere et al. |
| 2013/0174026 A1 | 7/2013 | Locke |
| 2013/0211855 A1 | 8/2013 | Eberle et al. |
| 2013/0238329 A1 | 9/2013 | Casella dos Santos |
| 2013/0238330 A1 | 9/2013 | Casella dos Santos |
| 2013/0238987 A1 | 9/2013 | Lutwyche |
| 2013/0251233 A1 | 9/2013 | Yang et al. |
| 2013/0268263 A1 | 10/2013 | Park et al. |
| 2013/0311201 A1 | 11/2013 | Chatfield et al. |
| 2014/0019531 A1 | 1/2014 | Czajka et al. |
| 2014/0025371 A1 | 1/2014 | Min |
| 2014/0039878 A1 | 2/2014 | Wasson |
| 2014/0072947 A1 | 3/2014 | Boguraev et al. |
| 2014/0072948 A1 | 3/2014 | Boguraev et al. |
| 2014/0089212 A1 | 3/2014 | Sbodio |
| 2014/0100846 A1* | 4/2014 | Haine ............... G06Q 10/067 704/9 |
| 2014/0100901 A1 | 4/2014 | Haine et al. |
| 2014/0100923 A1 | 4/2014 | Strezo et al. |
| 2014/0143720 A1 | 5/2014 | Dimarco et al. |
| 2014/0149107 A1 | 5/2014 | Schilder |
| 2014/0164303 A1 | 6/2014 | Bagchi et al. |
| 2014/0164304 A1 | 6/2014 | Bagchi et al. |
| 2014/0188477 A1 | 7/2014 | Zhang |
| 2014/0278358 A1 | 9/2014 | Byron et al. |
| 2014/0281935 A1 | 9/2014 | Byron et al. |
| 2014/0281951 A1 | 9/2014 | Megiddo et al. |
| 2014/0297268 A1 | 10/2014 | Govrin et al. |
| 2014/0316768 A1 | 10/2014 | Khandekar |
| 2014/0375466 A1 | 12/2014 | Reiter |
| 2014/0379322 A1 | 12/2014 | Koutrika et al. |
| 2014/0379378 A1 | 12/2014 | Cohen-Solal et al. |
| 2015/0006437 A1 | 1/2015 | Byron et al. |
| 2015/0032443 A1 | 1/2015 | Karov et al. |
| 2015/0081307 A1 | 3/2015 | Cederstrom et al. |
| 2015/0081321 A1 | 3/2015 | Jain |
| 2015/0095015 A1 | 4/2015 | Lani et al. |
| 2015/0106307 A1 | 4/2015 | Antebi et al. |
| 2015/0142418 A1 | 5/2015 | Byron et al. |
| 2015/0142421 A1 | 5/2015 | Buurman et al. |
| 2015/0154359 A1 | 6/2015 | Harris et al. |
| 2015/0163358 A1 | 6/2015 | Klemm et al. |
| 2015/0169522 A1 | 6/2015 | Logan et al. |
| 2015/0169548 A1 | 6/2015 | Reiter |
| 2015/0169659 A1 | 6/2015 | Lee et al. |
| 2015/0169720 A1 | 6/2015 | Byron et al. |
| 2015/0169737 A1 | 6/2015 | Bryon et al. |
| 2015/0179082 A1 | 6/2015 | Byron et al. |
| 2015/0227508 A1 | 8/2015 | Howald et al. |
| 2015/0242384 A1 | 8/2015 | Reiter |
| 2015/0261744 A1 | 9/2015 | Suenbuel et al. |
| 2015/0261836 A1 | 9/2015 | Madhani et al. |
| 2015/0279348 A1 | 10/2015 | Cao et al. |
| 2015/0310013 A1 | 10/2015 | Allen et al. |
| 2015/0310112 A1 | 10/2015 | Allen et al. |
| 2015/0310861 A1 | 10/2015 | Waltermann et al. |
| 2015/0324343 A1 | 11/2015 | Carter et al. |
| 2015/0324347 A1 | 11/2015 | Bradshaw et al. |
| 2015/0324351 A1 | 11/2015 | Sripada et al. |
| 2015/0324374 A1 | 11/2015 | Sripada et al. |
| 2015/0324413 A1 | 11/2015 | Gubin et al. |
| 2015/0325000 A1 | 11/2015 | Sripada |
| 2015/0326622 A1 | 11/2015 | Carter et al. |
| 2015/0331845 A1 | 11/2015 | Guggilla et al. |
| 2015/0331846 A1 | 11/2015 | Guggilla et al. |
| 2015/0332670 A1 | 11/2015 | Akbacak et al. |
| 2015/0347400 A1 | 12/2015 | Sripada |
| 2015/0356127 A1 | 12/2015 | Pierre et al. |
| 2015/0363363 A1 | 12/2015 | Bohra et al. |
| 2015/0363364 A1 | 12/2015 | Sripada |
| 2015/0363382 A1 | 12/2015 | Bohra et al. |
| 2015/0363390 A1 | 12/2015 | Mungi et al. |
| 2015/0363391 A1 | 12/2015 | Mungi et al. |
| 2015/0371651 A1 | 12/2015 | Aharoni et al. |
| 2016/0019200 A1 | 1/2016 | Allen |
| 2016/0027125 A1 | 1/2016 | Bryce |
| 2016/0055150 A1 | 2/2016 | Bird et al. |
| 2016/0132489 A1 | 5/2016 | Reiter |
| 2016/0140090 A1 | 5/2016 | Dale et al. |

FOREIGN PATENT DOCUMENTS

| | | |
|---|---|---|
| AU | 2013201755 A1 | 9/2013 |
| AU | 2013338351 A1 | 5/2015 |
| CA | 2577721 C | 3/2006 |
| CA | 2826116 C | 3/2006 |
| CN | 103999081 A | 8/2014 |
| CN | 104182059 A | 12/2014 |
| CN | 104881320 A | 9/2015 |
| EP | 1336955 B1 | 8/2003 |
| EP | 2707809 A1 | 3/2014 |
| EP | 2750759 A1 | 7/2014 |
| EP | 2849103 A2 | 3/2015 |
| GB | 2518192 A | 3/2015 |
| JP | S61221873 A | 10/1986 |
| JP | 2004021791 A | 1/2004 |
| JP | 2014165766 A | 9/2014 |
| WO | WO 2000/074394 A2 | 12/2000 |
| WO | WO 2002/031628 A3 | 4/2002 |
| WO | WO 2002/073449 A1 | 9/2002 |
| WO | WO 2002/073531 A1 | 9/2002 |
| WO | WO 2007/041221 A1 | 4/2007 |
| WO | WO 2009/014465 A2 | 1/2009 |
| WO | WO 2010/049925 A2 | 5/2010 |
| WO | WO 2010/051404 A1 | 5/2010 |
| WO | WO 2012/071571 A2 | 5/2012 |
| WO | WO 2013/009613 A1 | 1/2013 |
| WO | WO 2013/042115 A2 | 3/2013 |
| WO | WO 2013/042116 A1 | 3/2013 |
| WO | WO 2013/177280 A1 | 11/2013 |
| WO | WO 2014/035402 A1 | 3/2014 |
| WO | WO 2014/098560 A2 | 6/2014 |
| WO | WO 2014/140977 A1 | 9/2014 |
| WO | WO 2014/187076 A1 | 11/2014 |
| WO | WO 2015/113301 A1 | 8/2015 |
| WO | WO 2015/148278 A1 | 10/2015 |
| WO | WO 2015/164253 A1 | 10/2015 |
| WO | WO 2015/175338 A1 | 11/2015 |
| WO | WO 2016/004266 A2 | 1/2016 |

OTHER PUBLICATIONS

Reiter, Ehud, et al. "Choosing words in computer-generated weather forecasts." Artificial Intelligence 167.1 (2005): 137-169.*

Portet, François, et al. "Automatic generation of textual summaries from neonatal intensive care data." Artificial Intelligence 173.7 (2009): 789-816.*

Gatt, Albert, et al. "From data to text in the neonatal intensive care unit: Using NLG technology for decision support and information management." Ai Communications 22.3 (2009): 153-186.*

Reiter, Ehud. "An architecture for data-to-text systems." Proceedings of the Eleventh European Workshop on Natural Language Generation. Association for Computational Linguistics, 2007.*

U.S. Appl. No. 13/186,346, filed Jul. 19, 2011; In re: Nichols et al., entitled *Method and Apparatus for Triggering the Automatic Generation of Narratives*.

U.S. Appl. No. 14/027,684, filed Sep. 16, 2013; In re: Sripada et al., entitled *Method, Apparatus, and Computer Program Product for User-Directed Reporting*.

U.S. Appl. No. 15/022,420, filed Mar. 16, 2016; In re: Mahamood, entitlted *Method and Apparatus for Document Planning*.

U.S. Appl. No. 15/074,425, filed Mar. 18, 2016; In re: Reiter, entitled *Method and Apparatus for Situational Analysis Text Generation*.

U.S. Appl. No. 15/093,337, filed Apr. 7, 2016; in re: Reiter, entitled *Method and Apparatus for Referring Expression Generation*, Oct. 26, 2016.

U.S. Appl. No. 15/093,365, filed Apr. 7, 2016; In re: Logan et al., entitled *Method and Apparatus for Updating a Previously Generated Text*.

(56) References Cited

OTHER PUBLICATIONS

International Search Report and Written Opeinion for Application No. PCT/IB2013/058131 dated Jul. 3, 2014.
Gatt, A. et al., *From Date to Text in the Neonatal Intensive Care Unit: Using NLG Technology for Decision Support and Information Management*, AI Communication (Jan. 1, 2009) 33 pages
Quinlan, J.R., *Induction of Decision Trees*, Machine Learning, Kluwer Academic Publishers, vol. 1. No. 1 (Jan. 1, 1986) 81-106
Reiter, E., *An Architecture for Data-To-Text Systems*, Proceedings of ENLG-2007 (Jun. 20, 2007) 8 pages.

* cited by examiner

TEXT GENERATION FROM CORRELATED ALERTS

TECHNOLOGICAL FIELD

Embodiments of the present invention relate generally to natural language generation technologies and, more particularly, relate to a method, apparatus, and computer program product for operator text generation.

BACKGROUND

Natural language generation (NLG) is sometimes referred to as a subfield of artificial intelligence and computational linguistics that focuses on the production of understandable texts in English or other understandable language. In some examples, a natural language generation (NLG) system is configured to transform raw input data that is expressed in a non-linguistic format into a format that can be expressed linguistically, such as through the use of natural language (e.g., the conversion from data to text). In some cases the data is high frequency numerical data. For example, raw input data may take the form of a value of a stock market index over time and, as such, the raw input data may include data that is suggestive of a time, a duration, a value and/or the like. Other examples, may include the generation of textual weather forecasts base on numerical weather prediction data. Therefore, an NLG system may be configured to input the raw input data and output text that linguistically describes the value of the stock market index; for example, "securities markets rose steadily through most of the morning, before sliding downhill late in the day." Importantly, for use in an NLG system, data must be analysed and interpreted in a way in which the analysis and interpretation can be linguistically communicated. For example, data that indicates the price of a stock market rising may be represent linguistically as rising, spiking or the like. A human may then make decisions based on how that human interprets rising versus spiking.

Data that is input into a NLG system may be provided in, for example, a recurrent formal structure. The recurrent formal structure may comprise a plurality of individual fields and defined relationships between the plurality of individual fields. For example, the input data may be contained in a spreadsheet or database, presented in a tabulated log message or other defined structure, encoded in a 'knowledge representation' such as the resource description framework (RDF) triples that make up the Semantic Web and/or the like. In some examples, the data may include numerical content, symbolic content or the like. Symbolic content may include, but is not limited to, alphanumeric and other non-numeric character sequences in any character encoding, used to represent arbitrary elements of information. In some examples, the output of the NLG system is text in a natural language (e.g. English, Japanese or Swahili), but may also be in the form of synthesized speech.

BRIEF SUMMARY

Methods, apparatuses, and computer program products are described herein that are configured to generate an operator text in response to an alarm that is either received from an alarm or alert system or that is self-generated based on an analysis of one or more data feeds. The method of an example embodiment may include determining whether an operator text is to be generated in response to a received alert condition by performing data analysis operations comprising: analyzing, using a processor, a primary data feed and at least one confirmatory data feed to identify one or more features; and determining based on the detection of a feature in the primary data feed or the at least one confirmatory data feed satisfies at least one predetermined constraint. The method may further include generating an output text that is displayable in a user interface that describes at least a diagnosis for the feature that satisfied that at least one predetermined constraint.

In some example embodiments, a computer implemented method is disclosed herein that includes determining whether an operator text is to be generated in response to a received alert condition by performing data analysis operations. In some examples, the data analysis operations may include: analyzing, using a processor, a primary data feed and at least one confirmatory data feed to identify one or more features; determining whether an alert condition in the primary data feed is confirmed by at least one confirmatory data feed, wherein the alert condition is validated in an instance in which the primary data feed and the confirmatory data feed satisfy a correlation threshold; determining whether the feature in the primary data feed is explainable by at least one diagnostic data feed; and traversing, using one or more features in the primary data feed or the at least one confirmatory data feed, a decision tree, wherein the decision tree is operable to determine that at least a portion of an operator text is to be generated in an instance in which a feature evaluates as true for at least one node of the decision tree. In further examples, the computer implemented method may include generating the operator text for at least one feature that evaluates as true by performing language generation operations. The language generation operations may include, but are not limited to: arranging one or more messages in a document plan data structure in an order in which they are to be linguistically described in the operator text, wherein each of the one or more messages are data structures that are linguistically describable using at least one of a word or phrase and are instantiated based on the one or more features in the primary data feed or the at least one confirmatory data feed; converting, using a processor, at least one of the one or more messages into a text specification data structure that represents one or more data structures that are representative of at least one syntactic constituent and syntactic feature of a sentence; and applying a grammar to the text specification data structure to generate the operator text that is displayable in a user interface, wherein the operator text describes at least a diagnosis based on the at least one diagnostic data feed for the feature that evaluated as true.

In some example embodiments, an apparatus is disclosed herein that includes at least one processor; and at least one memory including computer program code, the at least one memory and the computer program code configured to, with the at least one processor, cause the apparatus to at least determine whether an operator text is to be generated in response to a received alert condition by performing data analysis operations. In some examples, the data analysis operations may be performed by: analyzing a primary data feed and at least one confirmatory data feed to identify one or more features; determining whether an alert condition in the primary data feed is confirmed by at least one confirmatory data feed, wherein the alert condition is validated in an instance in which the primary data feed and the confirmatory data feed satisfy a correlation threshold; determining whether the feature in the primary data feed is explainable by at least one diagnostic data feed; and traversing, using one or more features in the primary data feed or the at least one confirmatory data feed, a decision tree, wherein the decision tree is operable to determine that at least a portion of an operator text is to be generated in an instance in which a feature evaluates as true for at least one node of the decision tree. In further examples, the apparatus may further be configured to generate the operator text for at least one feature that evaluates as true by performing language generation operations. The language generation operations are performed by arranging one or more messages in a document plan data structure in an order in which they are to be linguistically described in the operator text, wherein each of the one or more messages are data structures that are linguistically describable using at least one of a word or phrase and are instantiated based on the one or more features in the primary data feed or the at least one confirmatory data feed; converting at least one of the one or more messages into a text specification data structure that represents one or more data structures that are representative of at least one syntactic constituent and syntactic feature of a sentence; and applying a grammar to the text specification data structure to generate the operator text that is displayable in a user interface, wherein the operator text describes at least a diagnosis based on the at least one diagnostic data feed for the feature that evaluated as true.

In some example embodiments, a computer program product is disclosed herein that includes at least one computer readable non-transitory memory medium having program code instructions stored thereon, the program code instructions which when executed by an apparatus cause the apparatus at least to determine whether an operator text is to be generated in response to a received alert condition by performing data analysis operations. In some examples, the data analysis operations may be performed by analyzing a primary data feed and at least one confirmatory data feed to identify one or more features; determining whether an alert condition in the primary data feed is confirmed by at least one confirmatory data feed, wherein the alert condition is validated in an instance in which the primary data feed and the confirmatory data feed satisfy a correlation threshold; determining whether the feature in the primary data feed is explainable by at least one diagnostic data feed; and traversing, using one or more features in the primary data feed or the at least one confirmatory data feed, a decision tree, wherein the decision tree is operable to determine that at least a portion of an operator text is to be generated in an instance in which a feature evaluates as true for at least one node of the decision tree. In further examples, the computer program product may further be configured to generate the operator text for at least one feature that evaluates as true by performing language generation operations. The language generation operations are performed by arranging one or more messages in a document plan data structure in an order in which they are to be linguistically described in the operator text, wherein each of the one or more messages are data structures that are linguistically describable using at least one of a word or phrase and are instantiated based on the one or more features in the primary data feed or the at least one confirmatory data feed; converting at least one of the one or more messages into a text specification data structure that represents one or more data structures that are representative of at least one syntactic constituent and syntactic feature of a sentence; and applying a grammar to the text specification data structure to generate the operator text that is displayable in a user interface, wherein the operator text describes at least a diagnosis based on the at least one diagnostic data feed for the feature that evaluated as true.

In some example embodiments, an apparatus is disclosed herein that includes means for determining whether an operator text is to be generated in response to a received alert condition by performing data analysis operations. In some examples, the means for data analysis operations may include means for analyzing a primary data feed and at least one confirmatory data feed to identify one or more features; means for determining whether an alert condition in the primary data feed is confirmed by at least one confirmatory data feed, wherein the alert condition is validated in an instance in which the primary data feed and the confirmatory data feed satisfy a correlation threshold; means for determining whether the feature in the primary data feed is explainable by at least one diagnostic data feed; and means for traversing, using one or more features in the primary data feed or the at least one confirmatory data feed, a decision tree, wherein the decision tree is operable to determine that at least a portion of an operator text is to be generated in an instance in which a feature evaluates as true for at least one node of the decision tree. In further examples, the apparatus may include means for generating the operator text for at least one feature that evaluates as true by performing language generation operations. The means for language generation operations may include, but are not limited to: means for arranging one or more messages in a document plan data structure in an order in which they are to be linguistically described in the operator text, wherein each of the one or more messages are data structures that are linguistically describable using at least one of a word or phrase and are instantiated based on the one or more features in the primary data feed or the at least one confirmatory data feed; means for converting at least one of the one or more messages into a text specification data structure that represents one or more data structures that are representative of at least one syntactic constituent and syntactic feature of a sentence; and means for applying a grammar to the text specification data structure to generate the operator text that is displayable in a user interface, wherein the operator text describes at least a diagnosis based on the at least one diagnostic data feed for the feature that evaluated as true.

BRIEF DESCRIPTION OF THE DRAWINGS

Figure 1:
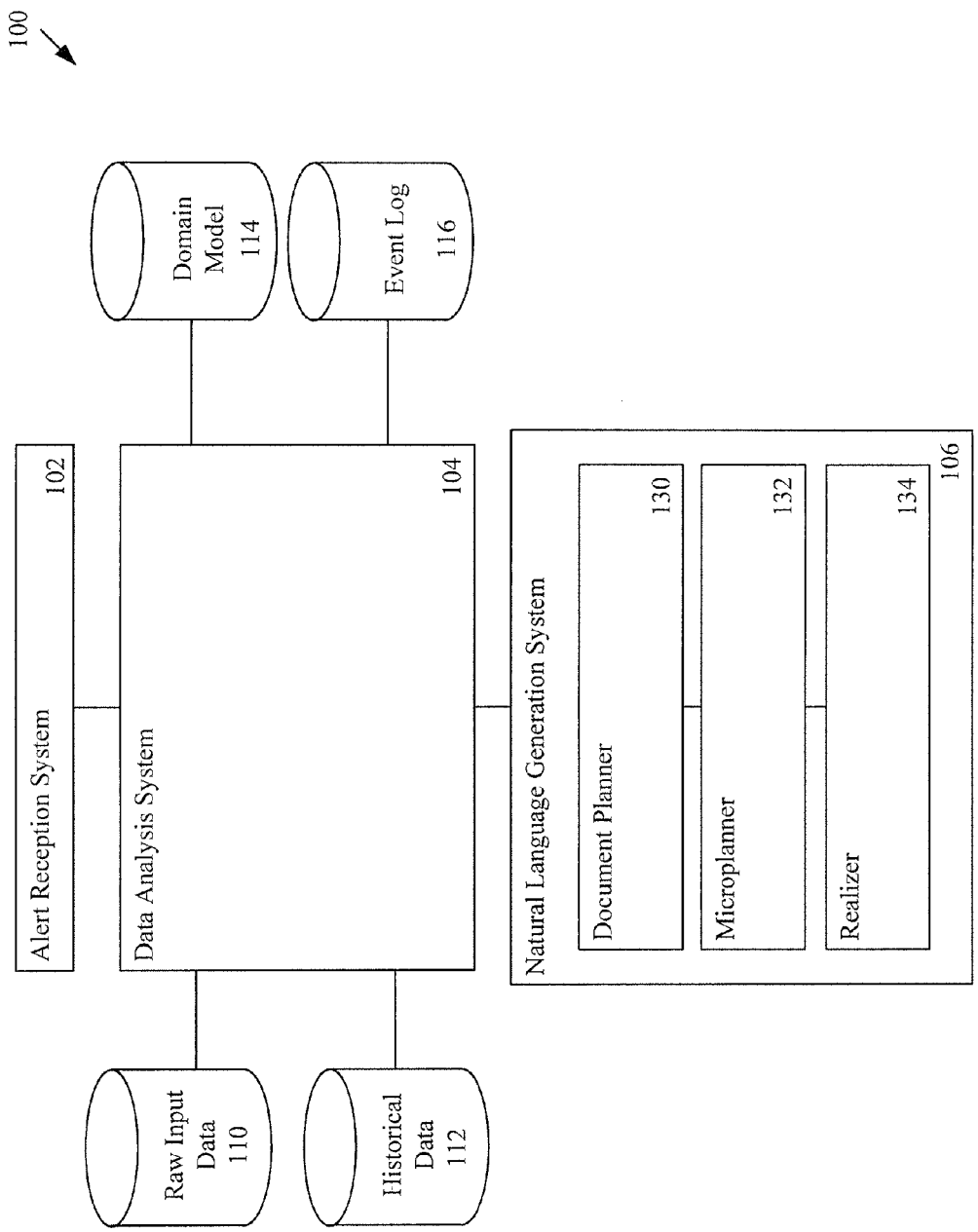
Figure 2A:
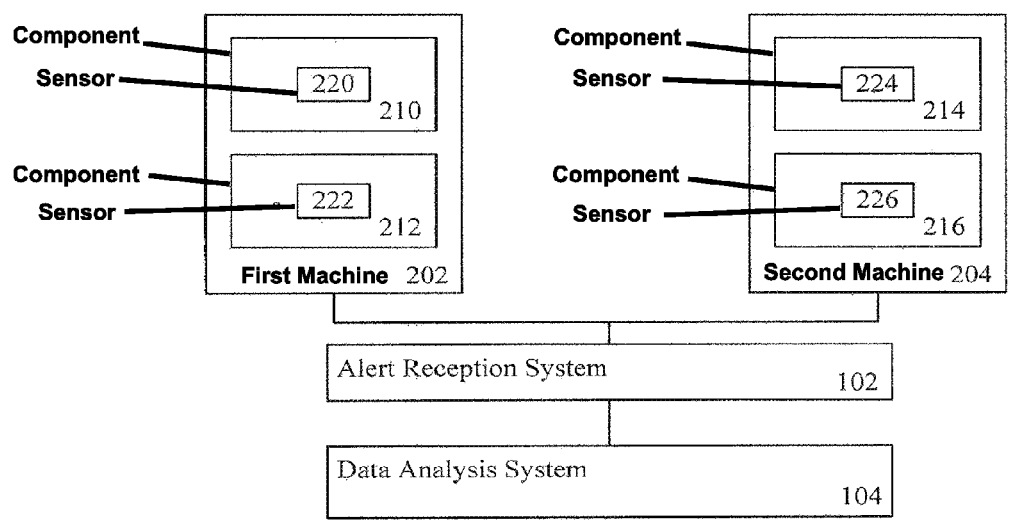
Figure 2B:
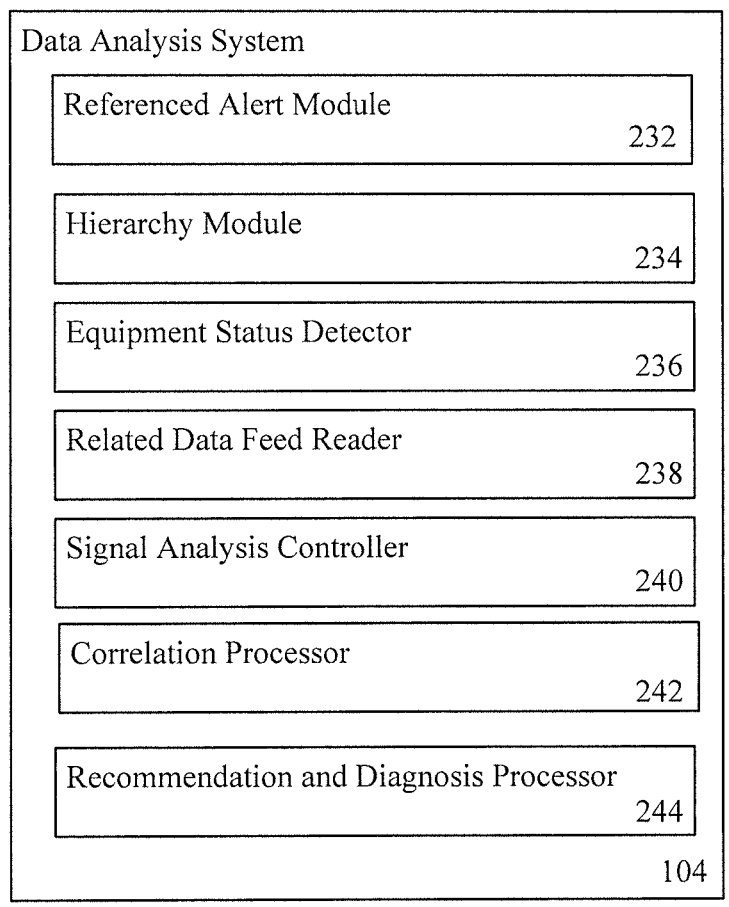
Figure 2C:
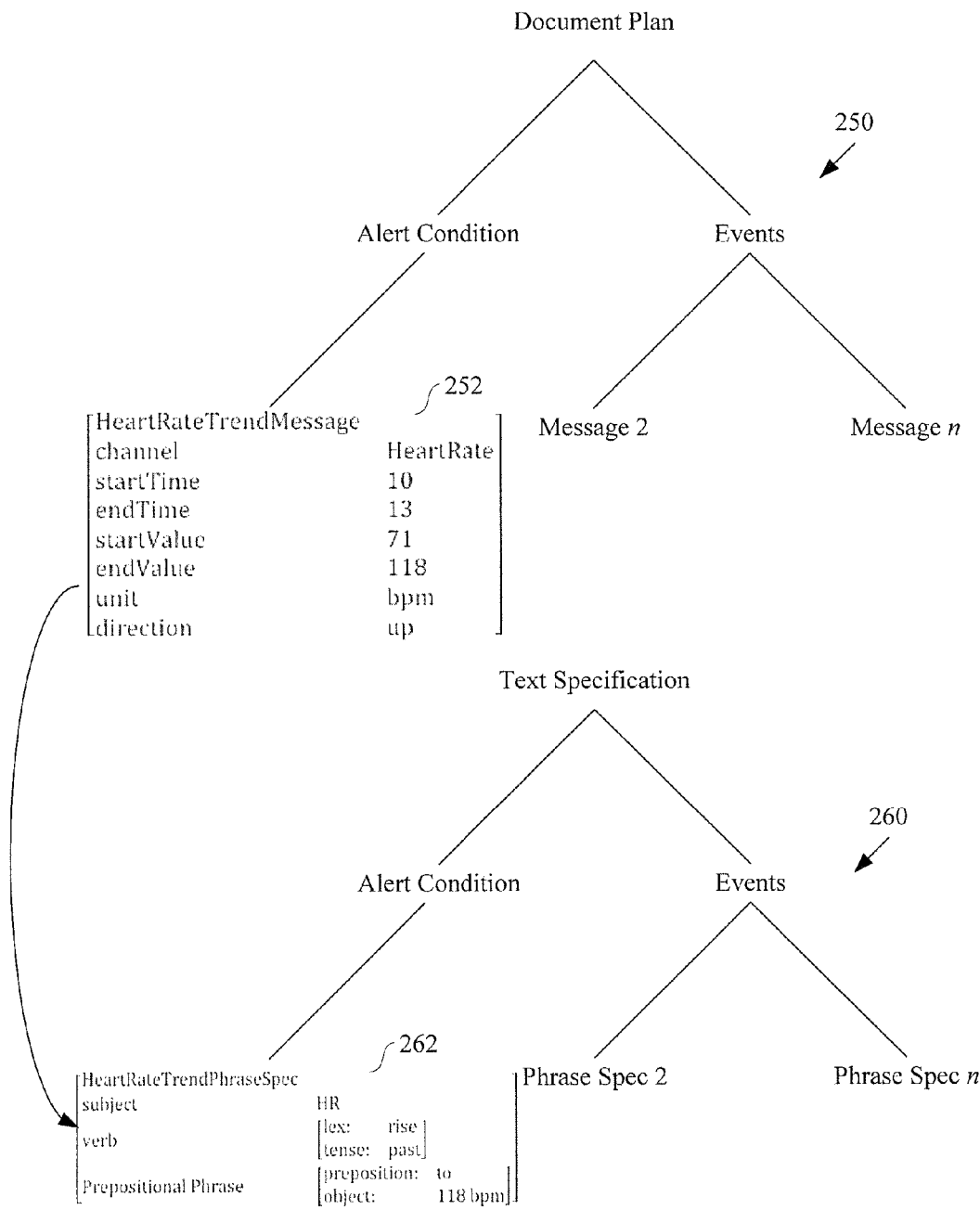
Figure 3:
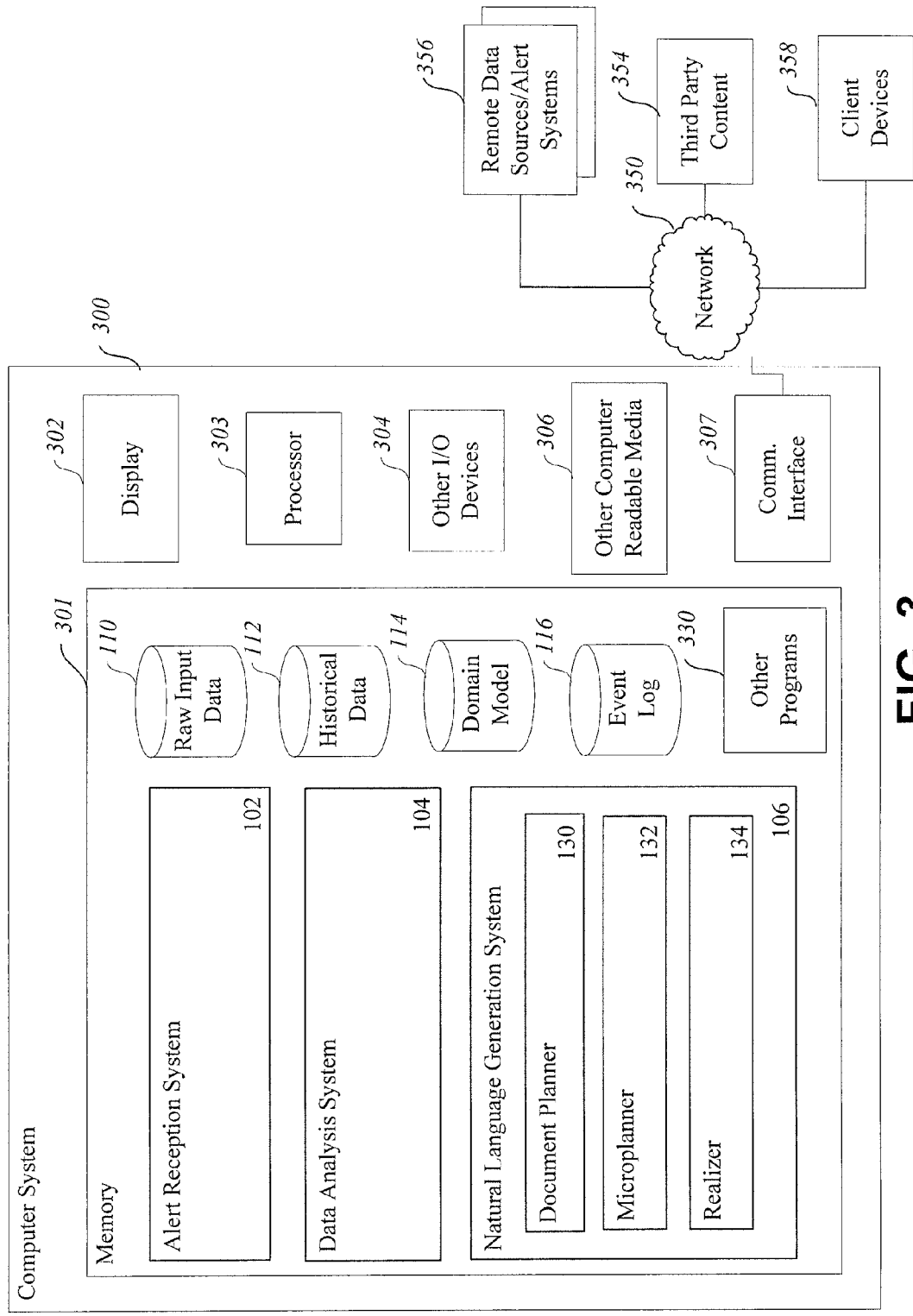
Figure 4:
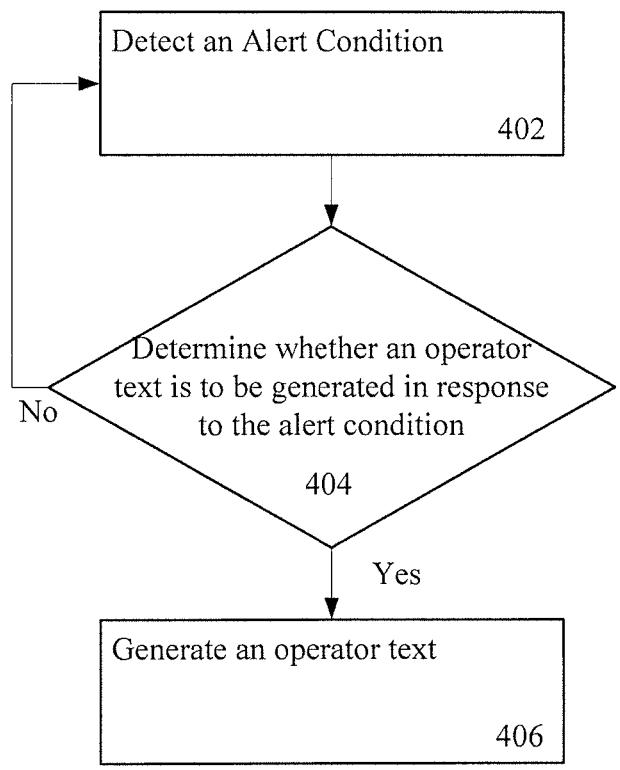
Figure 5:
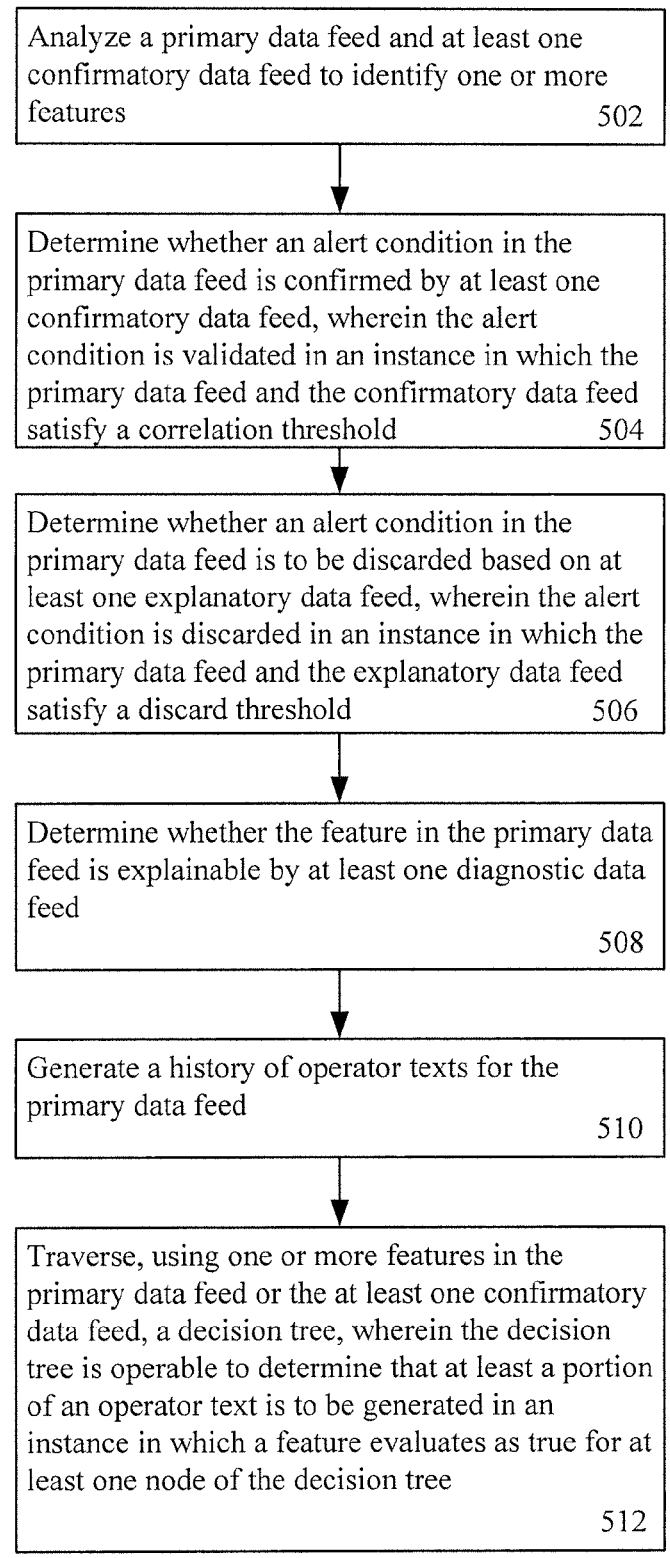
Figure 6:
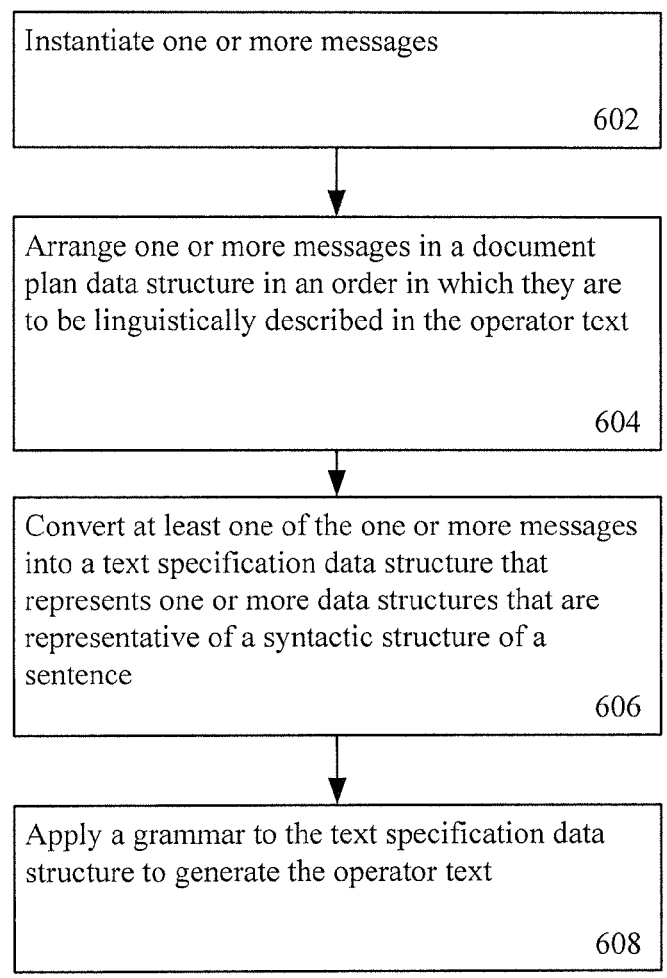

Having thus described embodiments of the invention in general terms, reference will now be made to the accompanying drawings, which are not necessarily drawn to scale, and wherein:

FIG. 1 is a schematic representation of an operator text generation environment that may benefit from some example embodiments of the present invention;

FIG. 2a illustrates an example alert monitoring system in an example machine monitoring domain according to some example embodiments described herein;

FIG. 2b illustrates an data analysis system according to some example embodiments described herein;

FIG. 2c illustrates an example document plan tree and a text specification in accordance with some example embodiments of the present invention;

FIG. 3 illustrates a block diagram of an apparatus that embodies an operator text generation environment in accordance with some example embodiments of the present invention; and FIGS. 4-6 illustrate flowcharts that may be performed by an operator text generation environment in accordance with some example embodiments of the present invention.

DETAILED DESCRIPTION

Example embodiments will now be described more fully hereinafter with reference to the accompanying drawings, in which some, but not all embodiments are shown. Indeed, the embodiments may take many different forms and should not be construed as limited to the embodiments set forth herein; rather, these embodiments are provided so that this disclosure will satisfy applicable legal requirements. Like reference numerals refer to like elements throughout. The terms "data," "content," "information," and similar terms may be used interchangeably, according to some example embodiments, to refer to data capable of being transmitted, received, operated on, and/or stored. Moreover, the term "exemplary", as may be used herein, is not provided to convey any qualitative assessment, but instead merely to convey an illustration of an example. Thus, use of any such terms should not be taken to limit the spirit and scope of embodiments of the present invention.

Overview

In some examples, one or more operators, technicians or the like may be tasked with responding to or otherwise addressing a series of alerts over a given time period. In particular examples, the operator may be responding to alerts that relate to machinery or equipment that could have a catastrophic result on people, infrastructure, other machines, platforms or the like if it were to fail. Given the importance of alert detection, the operator is generally inundated with alarming systems, data output system (dials, warning lights, graphs, indicators or the like) and various other outputs. As such, the operator may become overwhelmed or may indeed not interpret or understand the data (or warning signs) that are being presented before him/her. In some example cases, constant alarms or intermittent alarms may result in an operator simply ignoring or not responding to alarms.

Indeed, the problem facing the operator is not only the ability to detect patterns, trends or signals in the data (e.g., high frequency sensor data) that signify a fault, but also then determining if he/she needs to take a particular action to stave off a catastrophe. Most operators do not have the training, experience, time or the like to identify these patterns, trends or signals (that may act as an early warning signal) and make the necessary decisions. In other examples, the operator may see an alarm signal, but may be unable to diagnose the problem within a critical time period. Another more troubling problem is that the operator may not deduce a fault even when the warning signs are showing in the data. Operators are faced with each of these problems in real time as they are generally responsible for multiple systems, personnel and/or the like over long and demanding shifts.

In many instances, an operator may be required to interpret data, symbols or information in order to make a decision or otherwise gain an understanding of a current context, a situation or an event. In order to make such a decision or to otherwise react to an event, an operator may need to obtain an awareness (e.g. situational awareness) of the current context, the situation or the event before taking an action. Situational awareness may be defined as the perception of environmental elements with respect to time and/or space, the comprehension of their meaning, and the projection of their status after some variable has changed, such as time, or based on the happening of an event such as an alarm or alert. In other words, situational awareness is a state achieved when information that is qualitatively and quantitatively determined as suitable for a particular purpose is made available to a user by engaging them in an appropriate information exchange pattern or mental model. Situational awareness involves being aware of what is happening in the vicinity of a person or event to understand how information, events, and/or one's own actions may impact goals and objectives, both immediately and in the near future. Situational awareness may also be related to the perception of the environment critical to decision-makers in complex, dynamic areas from aviation, air traffic control, power plant operations, military command and control, engineering, machine monitoring, oil and gas, power plant monitoring, nuclear energy and emergency services such as firefighting and policing. The lack of or inadequate situational awareness has been identified as one of the primary factors in accidents attributed to human error.

Operators, technicians, nurses, and many other users in the modern world spend a great deal of time reacting to computer-generated alarms, alerts, and other indications, which result in a high false-positive rate. In some cases the false positive rate may be over 99%. One extreme example may be found with respect to airport baggage-screeners, where most screeners never see a valid alert in their entire working career. Identifying rare events is a difficult thing for users to do well, because the human brain is not well-suited to dealing with this kind of situation. For example, if a user has only ever seen or generally only sees certain alarms as false positives, the user may have a tendency to assume that all similar future alarms will also be false positives. Such cases occur, especially in instances in which operators deal with a large number of alarms, and, as such, may only have a few minutes for each individual alarm.

As such, the methods, apparatus, and computer program products described herein are configured to process incoming data into one or more data feeds and generate a diagnosis of a particular fault and actionable instructions for that operator to resolve the particular fault. In some examples, the operator may be operating on an oil extraction platform, operating an airplane, monitoring a patient, watching stock data or the like. In the case of the oil platform operator, the methods, apparatus, and computer program products described herein are configured to communicate with that operator so that operator is able to respond and address a problem or alert condition that is to occur (e.g., a piece of machinery may fail) within a given time period, such as within 30 minutes. Additionally, not only must that operator be alerted, but any such alert, such as the text generated by the methods, apparatus, and computer program products described herein, is configured to provide analytics, such as interpretation of an alarm system, an equipment failure diagnosis, a recommendation or the like. Additionally, the methods, apparatus, and computer program products described herein may also be designed to generate a text only for those critical alerts to avoid spamming, overwhelming or otherwise distracting the operator.

As described herein, the methods, apparatus, and computer program products are operable to solve or otherwise address the aforementioned problems by generating an output text in response to an alarm that is either received from an alarm or alert system or that is self-generated based on an analysis of one or more data feeds. The methods, apparatus, and computer program products described herein may then analyze one or more data feeds (e.g. one or more data feeds generated by sensors attached to machinery) to diagnose the fault and ultimately linguistically describe that diagnosis and provide, in some cases, recommendations, situational analysis and/or the like in an output text.

Advantageously, and in some examples, the output text that is generated by the methods, apparatus, and computer program products described herein is concise, reliable and tailored to the operator (e.g., based on domain rules, operator education level, context and/or the like). In some examples, the output text provides the operator with a decision or course of action so that the operator is no longer required to make a decision, but instead may act (e.g., shutdown compressor A, activate backup cooling system G, etc.). Advantageously, the operator text is designed to be constrained by a predetermined number of characters to ensure that the operator will read and address the fault without extraneous distractors in the text.

In order to generate the output text, an NLG architecture may be used that is tuned or otherwise designed for the generation of an operator text. As is described herein, the NLG system is operable to process data in the form of high frequency numerical data, such as a data feed received from a temperature sensor that is monitoring a compressor, and transform one or more observations or abstractions (e.g., features) taken from the high frequency numerical data into a linguistic representation of that data. Alternatively or additionally, the NLG system described herein may be configured to generate texts, such as operator texts, engineer texts, situational awareness texts, alert validation texts and/ or the like for the following non-exclusive list of oil platform equipment: reservoirs (e.g., modeling, well production forecasting, drainage performance, drive performance, gas cap maintenance, injection profiling and/or the like), wells (e.g., performance management, integrity assurance, completion integrity, inflow/outflow, impairment prediction and/or the like), oil plant (rotating equipment surveillance, strainers and filters, water quality monitoring, injection pump surveillance, injector profiling and/or the like), gas plant (compressor monitoring, dehydration, vapor recovery, gas quality assurance and/or the like), utilities (e.g., power generation, control system performance, control and safety, valve performance and/or the like), drilling (pore pressure prediction, real time drilling information, trouble avoidance, borehole safety, well control and/or the like), and/or the like.

In other words, the methods, apparatus, and computer program products described herein are configured to manipulate data that is stored in a memory of a computing system to transform or otherwise represent that data in natural language. For example, the data may be interpreted as illustrating a temperature rising, a temperature spiking, or a temperature sustaining a dangerous level for a period of time. In addition to simply providing a linguistic description of data trends or features, the output texts may also include a linguistic description of related machinery, a historical analysis of this type of alert in this machine or related machine, context (such as weather) that may be effecting the current alert or the like.

Operator Text Generation Overview

In some examples, and in order to generate an output text (e.g., operator text), the methods, apparatus, and computer program products as described herein may be configured to monitor one or more data feeds. These data feeds may be generated from sensors that are monitoring one or more pieces of equipment, may be data that is captured in stock trades, weather prediction data or the like. In some cases, the methods, apparatus, and computer program products described herein are operable to detect a trend in the one or more data feeds that is indicative of an alert condition. In other cases, the alert condition may be identified based on the activation of an alarm, the receipt of alarming indication or the like.

In response to the identification of an alarm condition related to a particular piece of equipment, the process described herein is configured to evaluate whether an output or operator text should be generated. In order to make such a decision, the methods, apparatus, and computer program products as described herein are operable to access a hierarchy (or other type of model that describes relationships between one or more data feeds) to determine the piece of equipment (e.g., the equipment or machine to which the sensor is attached) that is experiencing the alarm condition. In some examples, other related sensors or data feeds may also be loaded and/or analyzed, they include, but are not limited to: data feeds from confirmatory data feeds (e.g., one or more data feeds derived from sensors that are monitoring the same item, equipment or the like), explanatory data feeds (e.g., one or more data feeds that may be used to explain a particular condition), diagnostic data feeds (e.g., data feeds that are used to diagnose a fault or issue on a piece of equipment, such as, for example, providing an indication whether the equipment on or off, indicative of a fault based on a pressure level satisfying a threshold, and/or the like) or the like.

In some example embodiments, the alert condition or fault may be verified using the related data feeds (e.g., confirmatory data feeds, explanatory data feeds, diagnostic data feeds or the like). For example, the methods, apparatus, and computer program products as described herein may determine whether the alert condition is a result of a harmless cause as explained by, in some examples, the explanatory data feeds. For example, a determination is made as to whether an increase in temperature is the result of an intentional increase in speed by the machine (e.g., the operator intentionally increased speed to increase production). In such an example, an operator likely would expect a temperature reading to rise in an instance in which the equipment is working harder (e.g., speed is increasing) and thus would not want an operator text because the machine is likely behaving normally. Additionally, the alert condition may be validated based on an analysis of confirmatory data feeds. The analysis of the confirmatory data feeds should be the same or similar as the primary data feed for the alert to be valid. For example, if the primary data feed (e.g., the data feed that caused or otherwise is the basis for the alert condition) indicates an increase in temperature, but the confirmatory data feed s indicate temperature is normal, the alert or primary data feed may be experiencing a sensor glitch. In such a case, the operator text would likely indicate the need to replace the sensor instead of a more serious problem.

In some example embodiments, a diagnostic data feed may also be analyzed. In such examples, the diagnostic data feed may indicate a problem or fault with a piece of equipment, a component of the equipment (e.g. a cooling system for a compressor), an entity or the like. In such cases an alert condition directed to high temperature may be a result of a failed cooling system or a cooling system that was not operating (e.g., the cooling system is switched off). As such, the diagnostic data feed may assist in developing a diagnosis and/or a recommendation to such a problem in an output text (e.g., directing an operator to activate the cooling system).

In some example embodiments, and in conjunction with a determination of a shutdown threshold, a determination may be made as to a time until failure occurs (e.g., system will overheat and fail in 25 minutes). In particular, based on the trend analysis, the methods, apparatus, and computer program products described herein may be operable to provide an output text that describes the time until critical or catastrophic event occurs.

In the event that the alert condition is verified, the methods, apparatus, and computer program products described herein are configured to diagnose the underlying cause of the alert condition (e.g., fault) and then generate an output text or operator text that provides a recommendation or solution that addresses or otherwise solves the fault. The generation of an output text is further described with respect to FIGS. 1-3 below.

Operator Text Generation System

FIG. 1 is an example block diagram of example components of an example operator text generation environment 100. In some example embodiments, the operator text generation environment 100 comprises an alert reception system 102, a data analysis system 104, a natural language generation system 106 and one or more data sources, such as, but not limited to, one or more of raw input data 110, historical data 112, a domain model 114 and/or an event log 116. The alert reception system 102, the data analysis system 104, and/or the natural language generation system 106 make take the form of, for example, a code module, a component, circuitry and/or the like. The components of the operator text generation environment 100 are configured to provide various logic (e.g. code, instructions, functions, routines and/or the like) and/or services related to the generation of operator texts. In particular, components of the operator text generation environment 100 are operable to linguistically describe input high frequency numerical data at a level that allows for an operator to understand an alert condition and take action to correct the alert condition.

In some example embodiments an alert reception system 102 is configured to receive an indication of an alert condition (e.g. an alert received from a source such as, but not limited to, another system, an alarm system, a monitoring system or the like), a violation of a constraint (e.g. a data value over a threshold, within a threshold for a period of time and/or the like), a user input or the like. The alert reception system 102 may in some example embodiments be in data communication with an alert monitoring system, machine monitoring systems, equipment monitoring server, alarm centers, sensors and/or the like. In examples in which the alert reception system 102 is in communication with a monitoring system, the alert reception system 102 may receive a report (e.g., metadata), that includes but is not limited to a report identifier, an identification of a machine, sensor or the like that is experiencing the alert, the type of alert, a description, a title, and dates for maintenance requests related to the alert and/or the date time group (e.g. a set of characters, usually in a prescribed format, which may express the year, the month, the day of the month, the hour of the day, the minute of the hour, and/or the time zone) for the alert. Other alert condition information may be received and/or otherwise accessed in an alert database or data store via an alert monitoring system. However, in some example embodiments, the methods, apparatus and computer products described herein may operate without an alert reception system and/or the alert reception system 102 may be embodied by the data analysis system 104.

Alternatively or additionally, the alert reception system 102 is further configured to gather information, such as via raw input data 110, historical data 112, event log 116 or the like, on the history of an alert condition over a particular time period; for example, how often has the alert condition been triggered, how long was the alert condition active, or how often was the alert validated or not validated, responses to the alert, maintenance activity or the like. In some examples, the alert reception system 102 may further identify if a maintenance request is currently pending for an alert condition and, if so, a current status of the maintenance request. Closed or completed maintenance requests may also be determined by the alert reception system 102. A time period used to search for historical information about the alert condition may be predetermined, set by a user, set according to a domain model and/or the like. In some examples, the time period may be configured to exclude intermittent alert condition activity as described herein.

Alternatively or additionally, the alert reception system 102 may further gather or otherwise access information and/or data that refers to the status of a machine or unit having the alert condition. The information and/or data includes but is not limited to the functionality of the machine or unit, current operation of components of the machine, dependency diagrams that indicate whether power, cooling or the like is being supplied, the most recent start or stop times, maintenance times and/or the like. For example, the alert reception system 102 may determine whether a machine or unit has been started or stopped in the last 24 hours.

Referring now to FIG. 2a, FIG. 2a illustrates an example alert monitoring system in an example machine monitoring domain according to some example embodiments described herein. FIG. 2a illustrates a first machine 202 and a second machine 204. The first machine may comprise component 210 having a sensor 220 and component 212 having a sensor 222. The second machine may comprise component 214 having a sensor 224 and component 216 having a sensor 226.

As is described herein, the machines 202 and 204, the components 210-216 and/or the sensors 220-226 may be defined in terms of relationships (e.g., based on an equipment hierarchy). For example sensor 220 may be related to sensor 222 with a relationship defined as the data generated by sensor 220 moves in the opposite direction of sensor 222 (e.g. 220 is falling and 222 is rising). Other relationships, such as a relation between sensor 220 and 224, may also be defined in some example embodiments. Each of the relationships may be given an importance and/or otherwise may be weighted based on the importance level of the relationship between the sensors, such as 220 and 222, components 210 and 212 and/or the like. Relationship and importance may be determined for each machine, component, sub component, sensor and/or the like. Metadata and/or an ontology may also be specified that includes a linguistic description or title for each component, sub component or the like.

Referring again to FIG. 1, in some example embodiments, the data analysis system 104 may be operable to analyze one or more data feeds to determine one or more linguistically describable trends, occurrences or the like in the data. Referring now to FIG. 2b, FIG. 2b illustrates that the data analysis system 104 may comprise one or more of a referenced alert module 232, a hierarchy module 234, an equipment status detector 236, a related data feed reader 238, a signal analysis controller 240, a correlation processor 242 and/or a recommendation and diagnosis processor 244.

In some example embodiments, the data analysis system 104 and/or the referenced alert module 232 may be configured to receive relevant data about an alert and gather any relevant metadata about the alert. In some examples, the alert condition is at least one of received from an alert monitoring system over a data communication link or is determined based on the violation of a predetermined constraint by the primary data feed. Based, on the detection of an alert condition, the referenced alert module 232 may input raw data segmented into one or more data feeds. The data feed is correlated, in some examples, to a particular sensor, group of sensors or the like. The one or more data feeds may be contained in or otherwise received from the raw input data 110.

In some example embodiments, the receipt or input of the one or more data feeds may occur in response to an alert condition, such as is indicated by or otherwise received in the alert from the alert reception system 102. Alternatively or additionally the data analysis system 104 or the referenced alert module 232 may be configured to receive or input the one or more data feeds continuously or semi-continuously and may determine an importance of the one or more data feeds (e.g., whether the data violates a constraint, satisfies a threshold and/or the like) in order to detect or otherwise determine the presence of an alert condition. In other words, in some example embodiments, the data analysis system 104, the referenced alert module 232 or the like may function as or otherwise embody the alert reception system 102 and/or an alert detection system.

The one or more data feeds (e.g., the raw data may include data such as, but not limited to, time series data that captures variations across time (e.g. profits, rainfall amounts, temperature or the like), spatial data that indicates variation across location (e.g. rainfall in different regions), or spatial-temporal data that combines both time series data and spatial data (e.g. rainfall across time in different geographical output areas)). The one or more data feeds may be provided in the form of numeric values for specific parameters across time and space, but the raw input data may also contain alphanumeric symbols, such as the RDF notation used in the semantic web, or as the content of database fields.

In some example embodiments, the data analysis system 104 or the referenced alert module 232 is further configured to determine a main or primary data feed. In some examples, a main or primary data feed may be selected based on a selection by a user, via a user interface, may be selected based on the happening of a condition such as, but not limited to, an alert, an alarm, an anomaly, a violation of a constraint, a warning, may be predetermined and/or the like (e.g., features). In some cases, the primary data feed is generally related to, for example, the raw input data and/or data feed that caused the alert condition.

In some example embodiments, the data analysis system 104, the hierarchy module 134 or the like is configured to access a hierarchy (e.g., a part-of-hierarchy) to identify or otherwise read information about the equipment that is related to the primary data feed. The hierarchy in some examples describes the relationship of a particular piece of equipment within a larger grouping of equipment. For example, a turbine may be a part of a helicopter which is part of a squadron, etc. As such, in an instance in which a primary data feed is identified (e.g., the data feed related to the sensor that detected a condition that caused the current alert condition), the piece of equipment is then identified in the hierarchy.

In some example embodiments, the equipment status detector 236 is configured is determine current and/or historical data for a particular piece of equipment. In some examples, the equipment status detector 236 may provide additional context or additional details for a particular piece of equipment or machine (e.g., the maintenance history for the machine, the usage history (e.g. time on line), the on/off times and/or the like).

In some example embodiments, a related data feed reader 238 is configured to load or otherwise access one or more related data feeds, one or more historical data feeds and/or the like based on the data received from the hierarchy module 134. In some example embodiments, the one or more related data feeds are loaded based on an identification of one or more confirmatory data feeds as defined by the accessed hierarchy. In some examples, the historical data feeds may be related to the primary data feed (e.g., the data feed providing the indication of the alert condition) or the one or more confirmatory data feeds. In some examples, the related data feeds reader may load or otherwise access one or more explanatory data feeds and/or one or more diagnostic data feeds.

Relationships between data feeds may be defined as important or unexpected or may represent anomalous behavior as defined by a qualitative model such as the domain model 114. In some examples, the domain model 114 is a representation of information about a particular domain. For example, a domain model may contain an ontology that specifies the kinds of objects, concepts and/or the like that may exist in the domain in concrete or abstract form, properties that may be predicated of the objects, concepts and the like, relationships that may hold between the objects concepts and the like, and representations of any specific knowledge that is required to function in the particular domain. In some examples, multiple domain models may be provided for a single domain. For example, domains may include, but are not limited to, medical, rotating machinery, oil and gas, logistics, news and reporting, industrial, power, weather, legal, financial, nuclear and/or the like.

In some examples, relationships may be defined with respect to one or more sensors, sensor types, monitoring equipment or the like as defined by the hierarchy. For example, an alert on a first sensor may have a relationship with a second sensor on the same machine or on other related machines. The relationship may further include an indication that the related sensor generally detects movement in the same direction as the primary sensor or that the related sensor generally moves in an opposite direction from the primary sensor. An importance level may be also be assigned to a particular sensor, such as by a user, the domain model or the like. In some examples, this importance level may be used to determine an importance of a particular sensor event. In some cases, one or more sensors may be indicated as always to be included in a text.

Alternatively or additionally, the method, apparatus and computer program product described herein may further provide and/or otherwise access a rule language that is configured to qualitatively specify expected relationships between data feeds (e.g. a primary data feed and one or more related data feeds). The rule language may further be configured to specify or otherwise indicate instances in which related data feeds, related events and/or the like are mentioned in an operator text. In some examples, the rules may be built via a user interface, using the rule language that may extract or otherwise receive information related to the data feeds and the relationships between them. In some cases the data feeds and/or relationships may be discovered by analyzing one or more data sources. The rule language may further provide information related to the context of one or more data feeds and alerts that may be generated or accessed based on those data feeds, for example equipment status, alert history, and status of similar equipment elsewhere. Alternatively or additionally, the rule language may be derived and/or tuned using supervised or unsupervised learning models.

In some example embodiments, the signal analysis controller 240 is configured to analyze the one or more data feeds provided by the primary data feed, the confirmatory data feeds, the explanatory data feeds, the diagnostic data feeds and/or the like. Initially, the signal analysis controller may be configured to determine one or more problems or inconsistencies with the one or more data feeds that may be indicative of an error or invalid data. In some cases, the data problems may be in the data feed itself, in other cases the data problems may be a result of a communications error. In some examples, the signal analysis controller 240 may detect missing data in an instance in which data was not received over a predetermined duration (e.g. exceeds the time in which values are reported). In other examples, a sensor's values may not have changed over a predetermined period before an alert condition was indicated; such a case may indicate a frozen data condition. Frozen data may be identified in an instance in which a machine or unit is determined to be running during a period (e.g. based on a determined equipment status), the sensors are float valued and/or the sensor is not excluded from the frozen check. In other examples, raw input data may be checked to determine if the values fall outside those physically possible (e.g. temperatures that would cause melting). Other verification may include error tokens, inconsistent values and/or the like.

In some example embodiments, the signal analysis controller 240 is configured to detect patterns and trends in the one or more data feeds that are derived from the raw input data and/or the historical data to provide a set of abstractions. For example, a time-series dataset may contain tens of thousands of individual records describing the temperature at various time points on a component piece of machinery over the course of a day with a sample once every two or three seconds. Trend analysis may then be used to identify that the temperature changes in a characteristic way throughout certain parts of the day. As such, the trend analysis is configured to abstract those changes over time into an abstraction that is representative of the change over time.

In some example embodiments, the signal analysis controller 240 may be configured to fit a piecewise linear model to the data received in the primary data feed, related data feed or the like. The fitting of the piecewise linear model may include filtering in some examples. For each trend in the raw input data, the signal analysis controller 240 may determine a start and/or end time values, qualitative direction (e.g. up, down, steady), qualitative stability (e.g. stable, unstable), threshold status (e.g. normal, high, low, unknown at start, end of trend and/or the like). The signal analysis controller 240 may be configured to perform the fitting of the piecewise linear model for one or more time scales; for example, over a short term (e.g. 6 hours) using the time of the alert condition to determine how the machine or unit was acting at the time the alert became active. A longer time period (e.g. 2 months) may also be analyzed. In some examples, the longer time period may ignore equipment off periods and/or the like.

The signal analysis controller 240 may alternatively or additionally then identify trends, spikes, steps, oscillations or other patterns in the data feeds to generate abstractions that summarize the patterns determined in the primary data feed and/or the other related data feeds. Alternatively or additionally, the data analysis system 104 may also be configured to perform pattern detection on the raw input data irrespective of data feeds or the receipt of an alarm condition.

In other example embodiments, the signal analysis controller 240 may determine whether an alert condition in the primary data feed is confirmed by at least one confirmatory data feed. For example, the alert condition may be confirmed if the behavior in the primary data feed is replicated, at least in part, by the behavior in the confirmatory data feed). Additionally or alternatively, the signal analysis controller may determine whether an alert condition in the primary data feed is to be discarded based on at least one explanatory data feed. For example, the alert condition may not be confirmed if the increase in temperature is a result of an intentional increase in speed by the machine. Additionally, the signal analysis controller 240 may determine whether the feature in the primary data feed is explainable by at least one diagnostic data feed. For example, a diagnostic data feed may report that the cooling system is disabled for a machine. As such, the temperature increase may be explained by the disabled cooling system and could be rectified by activating the cooling system.

By way of example, and in an instance in which a temperature alert has been received, the signal analysis controller 240 may determine if the pattern or feature (increase, decrease or stable) of the primary data feed is explained by explanatory data feeds. If the main data feed is not explained by the explanatory data feeds, the signal analysis controller 240 may determine if the primary data feed and the confirmatory data feeds are correlated. If the primary data feed and its confirmatory data feeds are correlated: the signal analysis controller 240 may look-up the cooling system that is currently configured to be related the system and return any fault associated with that cooling system.

In some examples, the correlation processor 242 may be operable to analyze and, in some examples, score the signal correlation between the primary data feed and the one or more of its related data feeds (e.g., confirmatory data feeds, explanatory data feeds, diagnostic data feeds and/or the like). Determining the signal correlation between the primary data feed and its related data feeds allows for the assessment of the operational condition preceding the alarms (e.g., an increase/decrease in production, the start of an equipment failure, etc.). Signal correlation quantifies the strength of a linear relationship between two signals. If no signal correlation exists between two signals, then there is no tendency for the values of the variables to increase or decrease in tandem. The implemented signal correlation function produces a matrix of correlation coefficients R, for a signal matrix (where each column represents a separate signal). The correlation coefficients may range from $-1$ to $1$, in some example embodiments. In other examples, correlation coefficients above a predetermined threshold (e.g., above 0.02) indicate that there is a positive linear relationship or correlation between the data columns. The signal correlation function also returns P, a matrix of p-values for testing the hypothesis of no correlation. Each p-value is the probability of getting a correlation as large as the observed value by random chance, when the true correlation is zero. If $P(i,j)$ is small, for example less than 0.05, then the correlation $R(i,j)$ is significant.

In some examples, the recommendation and diagnosis processor 244 may be operable to determine whether to generate a text, and if so, what type of a recommendation or diagnosis to include in that text. In some examples, in order to determine whether an operator text is to be generated a decision tree, a machine learning model or the like may be used. In the decision tree embodiment, a series of if statements may be defined (and may ultimately be traversed) that identify one or more problems, features, patterns or the like (e.g., indication in the data that violate a constraint or the like) that if evaluated as true would trigger a text. In other examples, a machine learning model may be trained such that the presence of one or more features (e.g., indications of events, patterns detected or like) would generate a score that signifies the likelihood that a text should be generated. In an instance in which that score satisfied an operator text threshold score, then the system may generate the text. In some cases, these embodiments may be informed or constrained by one or more business rules.

In some examples, recommendations are built through a series of Decision Points. A Decision Point is a check that can be true or false. For example, the "BeingShutdown" decision point recommends that nothing should be done if the equipment is being currently shut down. In example embodiments herein, Decision Points enable the recommendation and diagnosis processor to determine whether a text to the operators. These are typically based on specific faults. For example, have all of the temperatures suddenly started rising together for no apparent reason? If yes, an operator text should be generated, for example, that indicates the problem as a clogged strainer issue. As such, should any decision point be true, a text may be generated for the operator in some example embodiments. In other examples, if the primary data feed is a temperature related data feed and it has an increasing trend, the system may decide there is a cooling issue and thus would generate an operator text with that diagnosis. If the primary data feed is related to a pressure tag and it has a decreasing trend, the system may determine there is a leakage issue and would generate an operator text with that diagnosis.

In some examples, a Decision Point is made up of four things: a certainty, an explanation, a piece of logic, and a set of features. The certainty of a Decision Point is a relative value that is used by the overall recommendation. Certainties may have values between 1 and −1. Problem Decision Points make the most use of their certainty. Their certainty is a relative measure of whether this Decision Point indicates a problem or not. A 1 means any time this Decision Point is true, there is definitely a problem. Similarly, −1 means there is no chance that there is a problem. The total probability that there is a problem is created by combining all of the different Problem Decision Points. One method for combining decision points includes, but is not limited to:
t=running total of certainty

```
for ( each decision point) {
    c = decision point certainty
    if ( t >= 0 && c >= 0){
        t = t + c * (1 - t)
    } else if ( t < 0 && c < 0){
        t = t + c * (1 + t)
    } else {
        t = t + c
            ─────────────
            1 - min(|t|, |c|)
    }
}
```

In some examples, action Decision Points use their certainty as a ranking system. The highest certainty Decision Point is used in the total recommendation, and the others are just included in the action reasons. Error Decision Points don't use their certainty. If there has been any problem in the recommendation processor, such is reported in the text. Error Decision Points should be set as 0. A Decision Point's explanation (e.g., a string which is used directly by the output text) is the explanation supplied to the reader for why it is/isn't a problem, why that action was recommended, why there may be an error, etc.

The logic of a Decision Point is what calculates whether the Decision Point is true or not. For example, a decision point related to temperature may include a test as to whether temperature is greater than a given threshold on a primary data feed and at least one secondary data feed. If the logic evaluates to true a Reason is created. A Reason is a message (e.g., described below) which wraps around the explanation. The features of a Decision Point are parameters that may be saved and used with machine learning that is described herein.

In some examples, the recommendation and diagnosis processor 244 may include a diagnostic model may be configured to determine or otherwise identify one or more possible causes of an alert condition. Based on the one or more possible causes of the alert condition, the diagnostic model may be further configured to determine which of the one or more data feeds should be examined to verify and/or disprove the one or more possible causes. For example, the diagnosis model may identify allergic reaction to medication as one reason for a spike in heart rate. It may also determine that if allergic reaction is suspected, a respiration rate data feed should be examined to verify and/or disprove this diagnosis, because respiration rate would become erratic if the underlying cause was allergic reaction. As such, in this example, respiration rate may be identified as a related data feed.

In some examples, machine learning may be used to build and/or modify the diagnostic model. In some examples, features for the machine learning model may be defined and may include: information about a data feed, results of historical decision point decisions, anything the decision points compare against a threshold and/or the like. Such a model can be trained by mapping the features to one or more historical alerts that have resulted in a service or maintenance request. As such, features can be selected based on their likelihood to result in an operator text. In some examples classifiers on subsets of the features (e.g., a J48 tree can be used). Because of a potential of an imbalance of services-non services, a costSensitive classifier can be used. This meta-classifier makes it so different false positives have different costs.

In some example embodiments, a natural language generation system, such as natural language generation system 106, is configured to generate phrases, sentences, text or the like which may take the form of natural language text. The natural language generation system 106 comprises a document planner 130, a microplanner 132 and/or a realizer 134. Other natural language generation systems may be used in some example embodiments, such as a natural language generation pipeline as described in Building Natural Language Generation Systems by Ehud Reiter and Robert Dale, Cambridge University Press (2000), which is incorporated by reference in its entirety herein.

In some examples, natural language generation system 106 may be configured to populate or otherwise instantiate one or more messages based on data or information in the primary data feed, the one or more related data feeds, the historical data, the contextual data feed, one or more events and/or the like. In some examples, messages are language independent data structures that correspond to informational elements in a text and/or collect together underling data in such a way that the underlying data can be linguistically expressed. In some examples, messages are created based on a requirements analysis as to what is to be communicated for a particular scenario (e.g. for a particular domain). A message typically corresponds to a fact about the underlying data (for example, the existence of some observed event)

that could be expressed via a simple sentence (although it may ultimately be realized by some other linguistic means). For example, to linguistically describe wind, a user may want to know a speed, a direction, a time period or the like, but also the user wants to know changes in speed over time, warm or cold fronts, geographic areas and or the like. In some cases, users do not even want to know wind speed; they simply want an indication of a dangerous wind condition. Thus, a message related to wind speed may include fields to be populated by data related to the speed, direction, time period or the like, and may have other fields related to different time points, front information or the like. The mere fact that wind exists may be found in the data, but to linguistically describe "light wind" or "gusts" different data interpretation must be undertaken as is described herein.

In some examples, a message is created by the natural language generation system 106 in an instance in which the data in the one or more data feeds warrants the construction of such a message. For example, a wind message would only be constructed in an instance in which wind data was present in the raw input data. Alternatively or additionally, while messages may correspond directly to observations taken from the raw data input, others, however, may be derived from the observations by means of a process of inference. For example, the presence of rain may be indicative of other conditions, such as the potential for snow at some temperatures. Alternatively or additionally, in some example embodiments, the natural language generation system 106 may embody all or portions of the data analysis system 104.

The concepts and relationships that make up messages may be drawn from an ontology (e.g. a domain model) that formally represents knowledge about the application scenario. For example, message structures may be defined by the domain model 114 based on a particular alert condition and/or the raw input data, such as but not limited to the primary and/or related data feeds. Messages may also be derived from another data structure, may be user defined and/or the like. Each type of message may also be represented by a message template, which expresses a relationship between instances of a number of concepts; the message template contains slots which may be filled in, or instantiated, using particular values that are derived from the raw input data.

As such, the natural language generation system 106 is configured to instantiate a plurality of messages based on the one or more data feeds. In order to determine the one or more messages, the importance level of each of the messages and relationships between the messages, the natural language generation system 106 may be configured to access the domain model 114 directly or indirectly via the data analysis system 104 or the like. The domain model 114 may contain information related to a particular domain or industry. In some examples, the domain model 114 may provide importance levels, single data feed limits related to normal behaviors in a domain (e.g. normal ranges), information related to anomalous behaviors and/or the like. In other examples, the domain model 114 may describe relationships between various events and/or phenomena in multiple data feeds. For example in a weather domain, a domain model may indicate or otherwise instantiate an extreme weather message in an instance in which wind speeds that are related to hurricane type events or temperatures that may cause harm to humans or other animals or may cause damage or interference to shipping are present in the data. The extreme weather message may then be labeled as important, whereas typical temperatures or a typical wind message may not be marked as important in some examples. Alternatively or additionally, the domain model 114 may be configured to contain or otherwise have access to the diagnostic model.

In some example embodiments, the natural language generation system 106 may be configured to annotate messages with an indication of their relative importance; this information can be used in subsequent processing steps or by the natural language generation system 106 to make decisions about which information should be conveyed and which information may be suppressed, such as by using the domain model 114. The natural language generation system 106 may assign an importance level to the one or more messages based on the pattern itself (e.g. magnitude, duration, rate of change or the like), defined constraints (e.g. defined thresholds, constraints or tolerances), temporal relationships between the pattern in the primary data feed and patterns in other related data feeds and/or the like. For example, a heart rate over 170 beats per minute, or 100 mile per hour winds, may be assigned a high level of importance. In some examples, messages that describe other patterns and/or constraints may be defined by the domain model 114. Alternatively or additionally, the natural language generation system 106 may also be configured to annotate messages with information about how they are related to each other; for example, the natural language generation system 106 might indicate that an event described in one message is assumed to have been caused by the event described in another message.

Using the importance level, the natural language generation system 106 may assign certain ones of the messages that describe or are otherwise are instantiated with patterns or other data in the primary data feed as including key events. A key event may be selected or otherwise identified based on a pre-determined importance level threshold, such as a threshold defined by a user, a constraint defined by the domain model 114, or the like. Alternatively or additionally, key events may be selected or otherwise identified based on those patterns in the primary data feed with the highest level of importance, those patterns that exceed or otherwise satisfy the pre-determined importance level threshold and/or the like. For example, a domain model or user preference may indicate that any messages having wind readings over 50 miles per hour may be designated as key events, whereas in other examples only a message with highest wind reading over a defined time period may be a determined to include a key event. In further examples, the importance level determination may be performed over a plurality of time scales that may be user defined, defined by the domain model or the like (e.g., one hour, one day, one week, one month and/or the like).

In some example embodiments, the natural language generation system 106 may also be configured to determine the importance of messages that describe patterns or events detected in one or more secondary or related data feeds. In some examples, the natural language generation system 106 may determine one or more messages that describe patterns or events in the related data feeds that overlap time-wise or occur within the same time period as the patterns in the primary data feed. For example, during the same time period as rain is detected, another data feed may detect temperature falling below the freezing point. The natural language generation system 106 may then mark the one or more messages that describe patterns or events in the related channels as important, expected, unexpected or as having or not having some other property based on the domain model 114. For example, the domain model may suggest that the one or more patterns in the related data feed were expected to rise as they did in the primary channel. By way of example, as winds are rising, a wave height may then be expected to rise. In other cases, the behavior of the one or more related channels may be unexpected or may be anomalous when compared to the behavior of the primary data feed.

The one or more messages may be marked as including significant events based on the importance level, domain model 114, constraints, user settings or the like. For example, messages that include patterns or events in the related data feed that have an importance level above a predetermined threshold defined by the domain model 114, a user or the like, and may be marked as including significant events. In some example embodiments, messages including unexpected patterns or messages may also be categorized as significant events as they are suggestive of a particular condition or fault. Other messages including patterns or events may be determined to be significant events based on one or more constraints on channel value (e.g. expected range of values or the like), data anomalies, patterns marked as neither expected or unexpected that satisfy an importance level, and/or the like.

In some example embodiments, the natural language generation system 106 may also be configured to determine the importance of messages built or otherwise instantiated using historical data, such as historical data 112, background information, event data, and/or the like. For example, historical data may contain information related to a previous alert condition and the actions taken or a result. Historical data may also provide indicators of the validity of an alert and/or provide additional information that may provide additional situational awareness or may assist diagnosing the fault.

In further example embodiments, the natural language generation system 106 may be configured to generate one or more messages based on determined or otherwise inferred events from the one or more data feeds, historical data, event data and/or the like. Events may include specific activities that may influence the one or more key events and/or may have caused the one or more significant events. In some examples, the one or more events may be inferred based in context with the one or more patterns in the primary and/or related data feeds. Alternatively or additionally events may be provided as a separate channel, such as a contextual data feed, in the raw input data 110, the event log 116 or may be provided directly to the natural language generation system 106. Alternatively or additionally, one or more messages may be generated based on the contextual data feed.

In some examples, the data analysis system 104, the data analysis system 104 or the like may receive raw input data, such as the data in the following table, that illustrates a primary data feed (e.g. heart rate) and a related data feed (e.g. respiration rate):

| Time | Heart Rate | Respiration Rate |
|---|---|---|
| 1 | 68 | 14 |
| 2 | 72 | 15 |
| 3 | 70 | 14 |
| 4 | 70 | 14 |
| 5 | 69 | 16 |
| 6 | 72 | 15 |
| 7 | 73 | 16 |
| 8 | 68 | 13 |
| 9 | 70 | 14 |
| 10 | 71 | 15 |
| 11 | 90 | 14 |
| 12 | 110 | 14 |
| 13 | 118 | 14 |
| 14 | 116 | 15 |
| 15 | 105 | 15 |
| 16 | 92 | 14 |
| 17 | 86 | 13 |
| 18 | 80 | 14 |
| 19 | 75 | 14 |
| 20 | 72 | 15 |
| 21 | 70 | 14 |
| 22 | 71 | 13 |
| 23 | 69 | 13 |
| 24 | 71 | 14 |

As is demonstrated by the raw input data in the table above, heart rate went above 115 beats per minute (bpm) at time point 13, thus causing an alert condition. As such, the alert reception system 102, the data analysis system 104 and/or the like may receive an indication of an alarm condition, such as by a patient monitoring system, patient monitoring equipment and/or based on the determination by the data analysis system 104 that the data indicates an alert situation. In response to the alert condition, the data analysis system 104 may cause the heart rate data feed to be the primary data feed. In other embodiments, a user, the domain model or the like may indicate that the primary data feed is the heart rate data feed. In some example embodiments, the data analysis system 104 may abstract or otherwise identify the rapid change of heart rate between time point 10 and time point 11 lasting to time point 15 for use by the natural language generation system 106.

The data analysis system 104 may also determine whether a secondary or related data feed (e.g. respiration rate) has a pattern (e.g. no change when a change is generally expected) in a corresponding time period. In some examples, the corresponding time period may be the same time period or may be a later time period when compared to the time period of the key events. Further, the corresponding time period may, in some examples, be defined by a domain model, such as domain model 114. In some example embodiments, the data analysis system 104 may abstract or otherwise identify the relatively flat and/or steady respiration rate between time point 10 and time point 15 for use by the natural language generation system 106.

In some example embodiments, the natural language generation system 106 is configured to generate one or more messages based on the raw input data in the one or more data feeds. As described herein, messages are language independent data structures that correspond to informational elements in a text and/or collect together underlying data in such a way that the underlying data can be linguistically expressed. Using the heart rate example, a message may include portions of the raw input data, to include abstractions of the data, but may also include additional distinctions necessary for the generation of text as the raw input data is likely to be insufficient for such a purpose. For example, a HeartRateSpike message may be instantiated using the raw input data and such a message may include: a time and relative variation in terms of heart rate change or peak heart rate, a time period and a direction. In some examples, another message may be generated on related channels, historic data, events and/or the like. In some examples, the HeartRateSpike message may be related to an Alert Message that contains information relating to the alert itself. For example, in an instance in which caffeine was applied prior to the heart rate spike, a message may be generated to identify such an event. Such a message may be an Event message that is instantiated with an event time and an event description, such as from the event log 116; for example, a message that indicates that caffeine had been orally administered prior to the spike in heart rate. Other messages such as Respiration Rate (e.g. respiration rate stable=yes), HeartRateAlertHistorical (e.g. previous alert condition quantity=2, time=yesterday), HeartRateHistorical (e.g. heart rate trend=no change, time period=10 days) may be instantiated to include information about the related data feeds and/or historical data. Alternatively or additionally, the natural language generation system 106, the document planner 130 and/or the like may be configured to generate the one or more messages.

The document planner 130 is configured to input the one or more messages that are generated and/or instantiated by the natural language generation system 106. The document planner 130 is further configured to determine how to arrange those messages to describe the patterns in the one or more data feeds derived from the raw input data. The document planner 130 may comprise a content determination process that is configured to select the messages, such as based on the decisions of the recommendation and diagnosis processor.

The document planner 130 may also comprise a structuring process that determines the order of messages to be included in a natural language text. In some example embodiments, the document planner 130 may access one or more text schemas for the purposes of content determination and document structuring. A text schema is a rule set that defines the order in which a number of messages are to be presented in a document. For example, an event message (e.g. medication injection) may be described prior to a key event message (e.g. rise in heart rate). In other examples, a significant event message (e.g. falling respiration rate) may be described after, but in relation to, a key event message (e.g. rise in heart rate). By way of further example a document plan may include, but is not limited to, an AlertMessage, a HeartRateSpike message and then a RespirationRate message. An Event message, HeartRateAlertHistorical message and HeartRateHistorical message may then follow in the example document plan.

In some examples, a document plan may take the form of:
Paragraph 1
    alert description, including setpoint information and temporal relation to recent restart (if any)
    description of previous stable period
    related data feeds with similar behavior (aggregated)
    related data feeds with different behavior (aggregated)
    Recommendation/analysis
    Actions
Paragraph 2
    Summary of other related operator texts
    Most recent related operator text The output of the document planner 130 may be a tree-structured object or other data structure that is referred to as a document plan. In an instance in which a tree-structured object is chosen for the document plan, the leaf nodes of the tree may contain the messages, and the intermediate nodes of the tree structure object may be configured to indicate how the subordinate nodes are related (e.g. elaboration, consequence, contrast and/or the like) to each other. A sample document plan may include, but is not limited to, document plan 250 of FIG. 2c. Document plan 250 may include but is not limited to one or more messages, such as message 252.

In some example embodiments, the microplanner 132 is configured to modify a document plan, to create a text specification for input into a realizer. As is shown in some examples, a document plan may contain one or more leaf nodes that contain messages. An example message may comprise a plurality of slots that contain a named attribute and a value (e.g. channel and "HeartRate"). A message may also comprise slots that contain a named attribute and a set of named attributes and their values. Other messages may include additional named attributes and values.

Initially and in some example embodiments, the text specification may include a tree structure that matches or is otherwise structured in the same or similar manner as a document plan tree. In some examples, one or more messages may be combined (e.g. one or more document plan nodes) to form a single phrase specification (e.g. to form a single text specification node). Each leaf node of a text specification may include a phrase specification with one or more empty elements. The microplanner 132 may be configured to populate those element values by applying genre parameters, lexicalization rules, reference rules, aggregation rules and the like.

In some example embodiments, the microplanner 132 may be configured to input a series of genre parameters that are representative of genre conventions. Genre conventions are rules about the use of language which apply throughout texts in that particular genre. In some examples, however, the rules may be overridden by a user, by lexicalization rules and/or the like. The genre conventions specify default behavior for the realizer so that these aspects of language use do not have to continually re-specified by a user. Examples of genre parameters include, but are not limited to, the particular tense (e.g. past, present or future) that should be used consistently throughout the text to be generated; a convention on the use of pronouns in the text to be generated; and/or a convention as to whether or not abbreviated names are to be used in the text to be generated. Alternatively or additionally, other elements of the phrase specification may be set by the one or more genre conventions.

Genre conventions may be applied by the microplanner 132 as a first step in the initialization of the phrase specification that corresponds to an individual message. In such a case, subsequently applied lexicalization rules may override the results of application of the genre parameters. Alternatively or additionally, genre parameters may be applied by the microplanner 132 once all the lexicalization rules have been applied to a given message. In such a case, the genre parameters are configured to populate the elements of the phrase specification that have not been specified or otherwise populated by the lexicalization rules. For example, a tense equal to past, may be set by genre parameter and/or a lexicalization rule.

In additional example embodiments, one or more lexicalization rules may be input. Lexicalization rules are rules that determine how the content of individual messages may be mapped into phrase specifications. In some examples, lexicalization rules may include, but are not limited to, message-level rules that are configured to apply to messages as a whole. Lexicalization rules may also be configured to apply to one or more slots within each message. For example, message-level rules may specify how the overall form of a phrase is to be constructed from the contents of a message (e.g. heart rate is rising, falling or staying steady). Slot-level rules may specify how specific kinds of entities that are present in a message should be described (e.g. heart rate is expressed via a prepositional phrase such as "to 118 bpm") or otherwise referred to (e.g. refer to a machine by its machine ID or full machine title). For example a message-level rule may map a name value and high rate value from a message to a phrase specification.

For a given domain, there may be at least one message-level lexicalization rule for each type of message in the ontology for that domain that may be applied b. The one or more lexicalization rules for a message type define one or more constraints that are configured to test the message itself, the discourse model (e.g. a model that is configured to store the relevant aspects of the discourse context, such as a list of entities mentioned in the text so far, and the lexicalization of the previous sentence in a text), parameters set by the document planner 130 and/or the genre parameters. In an instance in which the one or more lexicalization rules matches the constraints, a default lexicalization rule may be defined for each message type and/or slot type.

In one example, a message-level rule may be configured to specify a canned text string to be used whenever a message of the specified type is received as input. For example, a GREETING message might result in the simple text string "Hello friend". Message-level lexicalization rules may also be configured to assign the contents of the slots of a message to particular syntactic constituents (e.g. a word or group of words that function as a single unit, such as a noun phrase, a verb phrase, a prepositional phrase or the like, within a hierarchical structure) in a sentence as represented by a phrase specification. For example, a lexicalization rule, or the one or more lexicalization rules, may be configured to specify the verb to be used to express a particular type of message, and slots in the message might be assigned to the subject and object positions in the sentence. In some examples, a user may allocate information in the one or more slots of a message to the elements of a phrase specification by using the following non-exhaustive list of syntactic constituents, subject: typically the first position in the sentence; verb: the main action described in the sentence; object: typically the position following the verb; indirectobject: used in those cases where a verb has three arguments, as in "John gave the cat a bath"; frontmodifier: used to provide information that will be placed at the beginning of the sentence, as in "yesterday, John gave the cat a bath"; premodifier: used to provide information that will be placed immediately in front of the verb, as in "John reluctantly gave the cat a bath"; postmodifier: used to provide information that will be placed immediately after the object, as in "John took a bus to the city" and/or the like. Alternatively or additionally, a slot-level rule may be configured to specify a canned text string when a slot of a specified type is received and/or specify a slot to be mapped to a particular syntactic constituent in a sentence as represented by a phrase specification.

Alternatively or additionally, a message-level rule may also specify particular syntactic features of the sentence to be generated, such as by overriding default values for those features either as provided by the realizer itself or by the genre parameters. Typical features include but are not limited to tense, which may be set to PAST, PRESENT or FUTURE; aspect, which may be set to PERFECTIVE or PROGRESSIVE; passive, which may be set to either TRUE or FALSE; negation and/or the like. In some example embodiments, a slot-level rule may specify a particular feature of a sentence to be generated, such as by overriding a default value. Alternatively or additionally, tense and aspect may be computed, such as by using a Reichenbachian model which is based on the time of the message (e.g. when the event described by the message happened), the time the text is generated, and/or a reference time. In some examples, reference time can be computed using one or more of the following non-exhaustive list: setting a reference time to the time of the previous message in the text specification, setting the reference time as the time of the first message expressed in a current paragraph and/or the like.

In some example embodiments, the microplanner may also apply slot-level rules. Slot-level rules may be applied to each slot in each message to enable the slot to be mapped to an element of a phrase specification. In some example embodiments, the message-level rules described herein may also be expressed as slot-level rules, allowing recursive embedding. However, in some examples the value of the slot itself may be used to fill corresponding element in a phrase specification.

In some examples, the microplanner is configured to determine whether two or more phrase specifications can be combined together linguistically to produce a more complex sentence. For example, one or more other phrase specifications may be combined with phrase specification to form a more complex sentence. In some examples, a reference system is configured to determine how to refer to an entity so that it can be unambiguously identified by the reader. For example, in a first sentence "John Smith" may be used where "he" or "his" may be used in subsequent sentences.

Alternatively or additionally, a slot-level rule may be executed. In such cases, the slot-level rule may specify how the value of the slot should be described based on the reference rules. Possible reference rules include, but are not limited to, StringValue: indicating that a string value associated with the object should be used to refer to the object; Named Entity: indicating that a predefined reference strategy for named entities should be used to refer to the object and may include the choice between a full name or description, a reduced form of description, or a pronoun, on the basis of information about the other entities that have been referred to in the text; NumericValue: indicating that a predefined strategy for referring to numeric values should be used; TimeValue: indicates that a predefined reference strategy for referring to time values should be used to refer to the object; DurationValue: indicating that a predefined reference strategy for referring to durations should be used to refer to the object; EnumValue: indicating how specific values of an enumerated type should be expressed and/or the like.

In some example embodiments, the microplanner may also use a slot-level rule to specify content for each of a number of syntactic constituents within a linguistic element that is to be realized as a noun phrase. For example, the following non-exhaustive example list of positions may be available: determiner, specifier, noun, modifier, premodifier, postmodifier and/or the like. In some examples, a slot-level rule may also contain conditions that determine its applicability; amongst other things, these may be used to determine when the rule should have a null output, resulting in the constituent being elided in the sentence being planned.

In some example embodiments, the microplanner may also use one or more slot-level rules to specify syntactic features. For example, a slot level rule may specify the following non-exhaustive example list of syntactic features: a pronominal (e.g. force a use of a pronoun), number (e.g. singular or plural), an indication of definite or indefinite and/or the like.

The output of the microplanner 132, in some example embodiments, is a tree-structured text specification whose leaf-nodes are phrase specifications, and whose internal nodes express rhetorical relations between the leaf nodes. A tree-structured text specification may include, but is not limited to text specification 260 of FIG. 2c, having one or more phrase specifications, such as phrase specification 262.

A phrase specification may correspond to a sentence or a sub-sentence fragment (e.g. a title) and are produced from one or more messages. A phrase specification is configured to contain one or more syntactic constituents (e.g. subject, verb, prepositional phrase and/or the like) and one or more syntactic features (e.g. tense).

A realizer 134 is configured to traverse the tree-structured text specification to express the tree-structured text specification in natural language. The realization process that is applied to each phrase specification in a text specification makes use of a grammar which specifies the valid syntactic structures in the language and further provides a way of mapping from text specifications into the corresponding natural language sentences. The output of the process is, in some example embodiments, a well-formed natural language text. In some examples, the natural language text may include embedded mark-up. The output of the realizer 134, in some example embodiments, is the operator text. The realizer may also output situational analysis text or a narrative that is configured to describe or otherwise summarize the one or more key events, the one or more significant events, the one or more contextual data feeds, and/or the one or more events.

By way of example, the realizer may output the following text in response to the text specification shown above:

John Smith's heart rate monitor sounded an alarm at 10.56 because his heart rate went above 115 beats per minute (bpm). His respiratory rate and oxygen saturation did not change. Caffeine, which can affect heart rate, had been orally administered to John at 10.54. This alarm had gone off twice yesterday, but in both cases heart rate quickly reverted to 70 bpm. John's heart rate has not shown any long-term upward or downward trends since he was admitted 10 days ago. John's heart rate increase was likely caused by the administration of the caffeine.

Alternatively or additionally and by way of further example, an operator text may take the form of:

Impact:
We expect a compressor shutdown on this platform in 30 minutes unless action is taken.
Reason for Escalation:
The alarm was triggered by a rising temperature and the related data feeds are displaying a similar behavior.
Diagnosis:
There may be a strainer issue.
Situational Analysis:
Platform Header Temperature rose steadily from 118° F. to 155° F. between a given time period. Engineering high setpoint was 156° F. when the alert triggered. Tank Temperature, GP ⅔ drain temperature, Gearbox High Speed Shaft DE Bearing Temperature and NDE Bearing Temperature have similar behavior.

Alternatively or additionally, the natural language generation system 106 may be configured to generate a graph to display one or more key events that are detected in a data feed. In some example embodiments, the graph may also include one or more significant events in one or more related feeds and/or events. In further examples, a time period or duration of the data shown in the graph may be selected such that the displayed graph illustrates the portion of the data feed that contains the one or more key events. The output graph is further configured to include textual annotations that provide a textual comment, phrase or otherwise is configured to explain, using text, the one or more key events, the one or more significant events and/or the events in a contextual data feed in natural language. In further examples, the textual annotations are generated from the raw input data and further are designed, in some examples, to textually describe identified patterns, anomalies and/or the context of the graph. In some examples, a narrative (e.g. situational analysis text) may be included with the graph that provides situational awareness or an overview of the data/patterns displayed on and/or off of the graph.

Alternatively or additionally, the environment 100, may be configured to generate different types of texts based on the same one or more data feeds in some examples, operator texts or situational awareness texts for engineers may be generated, business level texts may be generated for executives or the like. In some examples, a situational analysis text may include, but is not limited to: an example paragraph containing one or more of an alert information message (e.g. alert name, unit, time), an intermittent alert message in an instance in which an alert has been on intermittently (e.g. start time), and/or an intermittent validation summary message in an instance in which the alert has been on intermittently and alert validation has been completed, such as by the data analysis system 104 (e.g. number of times validated, number of times not validated). An example paragraph relating to the behavior of the sensor via the raw input data. This paragraph may include but is not limited to messages related to data problems if there are data problems, messages related to primary trends in the form of key events and/or a machine status message (e.g. on/off, on duration, multiple starts or the like). In an instance in which the document planner 130 is configured to provide a recommendation, one or more recommendation messages and/or explanations may be included by the document planner 130.

Alternatively or additionally, the situational analysis text may include one or more of a concurrent alerts summary, in an instance in which there are similar alerts on related units; a similar alert summary; active maintenance request messages in an instance in which there are active maintenance requests for this alert condition on the machine (e.g. number, status) and related maintenance request messages in an instance in which there are active maintenance requests for this alert condition on related units; a data problems message and/or previous history messages.

In some example embodiments, the situational analysis text may include, but is not limited to, messages describing a key event in the primary data feed, key event of a paired sensor (e.g. sensors monitoring the same component), messages related to a machine startup in an instance in which the key event is related to the start of a machine; messages related to related data feeds with an importance level exceeding a threshold (e.g. significant messages) sorted based on direction, paired sensors, sensor type or the like; messages related to unexpected behavior (e.g. significant events) also based on direction, paired sensors, sensor type or the like; and/or other messages related to events (e.g. an event summary), related feeds, historical information and/or the like. A situational analysis text may further include messages as described herein for each time duration included.

In further example embodiments, a situational analysis text and/or an operator text may include a recommendation with a supporting explanation. For example, a recommendation may include a recommendation to create a maintenance service on a particular piece of machinery, and the supporting explanation may include, but is not limited to, describing via text that there are no current maintenance requests for a particular machine as well as describing that previous alert conditions similar to a current alert condition resulted in a need for a maintenance request. Other recommendations, such as future actions, recommended investigations and/or the like may be provided via text with an explanation or data to support or otherwise provide context for the recommendation. Alternatively or additionally, the recommendation may take the form of a diagnosis of the alert condition. In such cases, a situational analysis text may include the diagnosis, based on a diagnostic model, one or more possible causes and/or an explanation of the diagnosis.

In some example embodiments, the NLG system that is described herein is an advanced computational linguistics application into which, in some examples, knowledge and expertise of experienced experts, machine learning models, analysis models and the like is permanently and continuously captured. In further examples, the NLG system described herein has the ability to continuously ingest and analyze current and historical data inputs from multiple, complex systems and technology platforms from any point in the service delivery stack (e.g., sensor data historian, alert monitoring system, equipment & alert metadata, engineer maintenance history, operator logs, diagnostic business rules and/or the like). In further still examples, and, from such inputs, write expert plain language (e.g., English narratives that provide instant support to operational decision making processes.

In some examples, the NLG system described herein is configured to input structured and unstructured data and information from multiple disparate sources and systems. The NLG system, in some examples, is then configured to replicate the thought processes of senior engineers to generate the highest priority information to be reported based on the historical context. The NLG system, in some examples, automatically writes rich and technically relevant, plain language summary reports that a reader would believe were written by an experienced engineer, operator, expert, analyst or the like based on what is important within the time period.

By way of example, the NLG system described herein, in some examples, is configured to generate and/or otherwise write reports that: speak in a defined "voice" in a consistent manner tailored to different audiences; is programmable for all languages, is exportable to any portal (e.g. user interface, communication medium or the like) and may be run based on alerts, periodic requests and or the like.

In some examples, an NLG system, such as the one described herein, may include input from various diverse data sources (e.g., sensor data historian, alert monitoring system, equipment and alert metadata, engineer maintenance history, operator logs, diagnostic business rules and/or the like). The example NLG engine may perform data analytics (e.g., such as based on domain knowledge, subject matter expertise, reasoning rules, interpretation rules and/or the like) to generate a message pool (e.g. atoms of informative content that can be used to tell a story). An example document planner may select and/or organize the various messages in the message pool (e.g., such as based on an importance assessment, a relevance assessment, genre conventions, story-telling rules and/or the like). The overall document plan may take the form of a contextually appropriate plan for the overall structure of the text. In some examples a microplanner (e.g., aggregation rules, semantic rules, reference conventions, lexical rules and/or the like) generates sentence plans (e.g., specifications for how information should be packaged into individual sentence). A linguistic realizer (e.g., syntax rules, morphological rules, formatting rules, orthographic rules and/or the like) may be used to generate the NLG output (e.g. decision support narratives, instant support for human decisions and actions, alert driven, periodic, operations, engineering and/or the like).

In some examples, the NLG system described herein is configured to analyze and prioritizes alerts generated by a monitoring system; combine pattern analysis, knowledge based reasoning and natural language processing; determine patterns in data, identify which of the patterns are most important and then analyzes what these patterns tell about the current operational situation. In some examples, the system may then generate expert, accurate, real time engineering and operational decision support recommendations and delivers them to onshore and offshore engineers and/or operators to action; may support day to day engineering and operational performance improvement and/or may, in some example, reduce the decision support process from hours to seconds.

Example System Architecture

FIG. 3 is an example block diagram of an example computing device for practicing embodiments of an example operator text generation system. In particular, FIG. 3 shows a computing system 300 that may be utilized to implement an operator text generation environment 100 having an alert reception system 102; a data analysis system 104; a natural language generation system 106 including, in some examples, a document planner 130, a microplanner 132 and/or a realizer 134; and/or an optional user interface (not shown). One or more general purpose or special purpose computing systems/devices may be used to implement the alert reception system 102, the data analysis system 104 and/or the natural language generation system 106. In addition, the computing system 300 may comprise one or more distinct computing systems/devices and may span distributed locations. In some example embodiments, the alert reception system 102, the data analysis system 104 and/or the natural language generation system 106 may be configured to operate remotely via the network 350. In some example embodiments, a pre-processing module or other module that requires heavy computational load may be configured to perform that computational load and thus may be on a remote device or server. For example, the data analysis system 104 may be accessed remotely. In some examples, operator text generation environment 100 may be offered using a software as a service model. Furthermore, each block shown may represent one or more such blocks as appropriate to a specific example embodiment. In some cases one or more of the blocks may be combined with other blocks. Also, the alert reception system 102, the data analysis system 104 and/or the natural language generation system 106 may be implemented in software, hardware, firmware, or in some combination to achieve the capabilities described herein.

In the example embodiment shown, computing system 300 comprises a computer memory ("memory") 301, a display 302, one or more processors 303, input/output devices 304 (e.g., keyboard, mouse, CRT or LCD display, touch screen, gesture sensing device and/or the like), other computer-readable media 305, and communications interface 306. The processor 303 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 3 as a single processor, in some embodiments the processor 303 comprises a plurality of processors. The plurality of processors may be in operative communication with each other and may be collectively configured to perform one or more functionalities of the operator text generation system as described herein.

The alert reception system 102, the data analysis system 104 and/or the natural language generation system 106 are shown residing in memory 301. The memory 301 may comprise, for example, transitory and/or non-transitory memory, such as volatile memory, non-volatile memory, or some combination thereof. Although illustrated in FIG. 3 as a single memory, the memory 301 may comprise a plurality of memories. The plurality of memories may be embodied on a single computing device or may be distributed across a plurality of computing devices collectively configured to function as the operator text generation system. In various example embodiments, the memory 301 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof.

In other embodiments, some portion of the contents, some or all of the components of the alert reception system 102, the data analysis system 104 and/or the natural language generation system 106 may be stored on and/or transmitted over the other computer-readable media 305. The components of the alert reception system 102, the data analysis system 104 and/or the natural language generation system 106 preferably execute on one or more processors 303 and are configured to generate operator texts, as described herein.

Alternatively or additionally, other code or programs 330 (e.g., an administrative interface, a Web server, and the like) and potentially other data repositories, such as data repository 340, also reside in the memory 301, and preferably execute on one or more processors 303. Of note, one or more of the components in FIG. 3 may not be present in any specific implementation. For example, some embodiments may not provide other computer readable media 305 or a display 302.

The alert reception system 102, the data analysis system 104 and/or the natural language generation system 106 are further configured to provide functions such as those described with reference to FIG. 1. the alert reception system 102, the data analysis system 104 and/or the natural language generation system 106 may interact with the network 350, via the communications interface 306, with remote data sources/alert systems 356 (e.g. remote reference data, remote performance data, remote aggregation data, remote alert systems and/or the like), third-party content providers 354 and/or client devices 358. The network 350 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX, Bluetooth) that facilitate communication between remotely situated humans and/or devices. In some instance the network 350 may take the form of the internet or may be embodied by a cellular network such as an LTE based network. In this regard, the communications interface 306 may be capable of operating with one or more air interface standards, communication protocols, modulation types, access types, and/or the like. The client devices 358 include desktop computing systems, notebook computers, mobile phones, smart phones, personal digital assistants, tablets and/or the like.

In an example embodiment, components/modules of the alert reception system 102, the data analysis system 104 and/or the natural language generation system 106 are implemented using standard programming techniques. For example, the alert reception system 102, the data analysis system 104 and/or the natural language generation system 106 may be implemented as a "native" executable running on the processor 303, along with one or more static or dynamic libraries. In other embodiments, the alert reception system 102, the data analysis system 104 and/or the natural language generation system 106 may be implemented as instructions processed by a virtual machine that executes as one of the other programs 330. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use synchronous or asynchronous client-server computing techniques. Also, the various components may be implemented using more monolithic programming techniques, for example, as an executable running on a single processor computer system, or alternatively decomposed using a variety of structuring techniques, including but not limited to, multiprogramming, multithreading, client-server, or peer-to-peer, running on one or more computer systems each having one or more processors. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the alert reception system 102, the data analysis system 104 and/or the natural language generation system 106, such as by using one or more application programming interfaces can be made available by mechanisms such as through application programming interfaces (API) (e.g. C, C++, C#, and Java); libraries for accessing files, databases, or other data repositories; through scripting languages such as XML; or through Web servers, FTP servers, or other types of servers providing access to stored data. The raw input data 110, historical data 112, the domain model 114 and/or the event log 116 may be implemented as one or more database systems, file systems, or any other technique for storing such information, or any combination of the above, including implementations using distributed computing techniques. Alternatively or additionally, the raw input data 110, historical data 112, the domain model 114 and/or the event log 116 may be local data stores but may also be configured to access data from the remote data sources/alert systems 356.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the alert reception system 102, the data analysis system 104 and/or the natural language generation system 106 may be implemented or provided in other manners, such as at least partially in firmware and/or hardware, including, but not limited to one or more ASICs, standard integrated circuits, controllers executing appropriate instructions, and including microcontrollers and/or embedded controllers, FPGAs, complex programmable logic devices ("CPLDs"), and the like. Some or all of the system components and/or data structures may also be stored as contents (e.g., as executable or other machine-readable software instructions or structured data) on a computer-readable medium so as to enable or configure the computer-readable medium and/or one or more associated computing systems or devices to execute or otherwise use or provide the contents to perform at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

Example Process Flow Diagrams

FIGS. 4-6 illustrate example flowcharts of the operations performed by an apparatus, such as computing system 300 of FIG. 3, in accordance with example embodiments of the present invention. It will be understood that each block of the flowcharts, and combinations of blocks in the flowcharts, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory 301 of an apparatus employing an embodiment of the present invention and executed by a processor 303 in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 4-6, when executed, convert a computer or processing circuitry into a particular machine configured to perform an example embodiment of the present invention. Accordingly, the operations of FIGS. 4-6 define an algorithm for configuring a computer or processor, to perform an example embodiment. In some cases, a general purpose computer may be provided with an instance of the processor which performs the algorithm of FIGS. 4-6 to transform the general purpose computer into a particular machine configured to perform an example embodiment.

Accordingly, blocks of the flowchart support combinations of means for performing the specified functions and combinations of operations for performing the specified functions. It will also be understood that one or more blocks of the flowcharts', and combinations of blocks in the flowchart, can be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included (some examples of which are shown in dashed lines in FIG. 4). It should be appreciated that each of the modifications, optional additions or amplifications described herein may be included with the operations herein either alone or in combination with any others among the features described herein.

FIG. 4 is a flow chart illustrating an example method for generating an operator text. As is shown in operation 402, an apparatus may include means, such as the alert reception system 102, the data analysis system 104, the processor 303, or the like, for detecting an alert condition. As is described herein an alert condition indication may be received from an alert monitoring system or may be generated by the data analysis system 104 based on a feature in the one or more data feeds. As is shown in decision operation 404, an apparatus may include means, such as the data analysis system 104, the processor 303, or the like, for determining whether an operator text is to be generated in response to the alert condition. Additional details with respect to determining whether an operator text is to be generated is described with respect to FIGS. 1-3 and 5. In an instance in which it is determined that an operator text is not to be generated, the process returns to operation 402. In an instance in which it is determined that an operator text is to be generated, as is shown in operation 406, an apparatus may include means, such as natural language generation system 106, the processor 303, or the like, for generating an operator text. Additional details with respect to determining whether an operator text is to be generated is described with respect to FIGS. 1-3 and 6.

FIG. 5 is a flow chart illustrating an example method for determining whether an operator text is to be generated in response to the alert condition. As is shown in operation 502, an apparatus may include means, such as the data analysis system 104, the processor 303, or the like, for analyzing a primary data feed and at least one confirmatory data feed to identify one or more features. As is shown in operation 504, an apparatus may include means, such as the data analysis system 104, the processor 303, or the like, for determining whether an alert condition in the primary data feed is confirmed by at least one confirmatory data feed, wherein the alert condition is validated in an instance in which the primary data feed and the confirmatory data feed satisfy a correlation threshold. As is shown in operation 506, an apparatus may include means, such as the data analysis system 104, the processor 303, or the like, for determining whether an alert condition in the primary data feed is to be discarded based on at least one explanatory data feed, wherein the alert condition is discarded in an instance in which the primary data feed and the explanatory data feed satisfy a discard threshold. As is shown in operation 508, an apparatus may include means, such as the data analysis system 104, the processor 303, or the like, for determining whether the feature in the primary data feed is explainable by at least one diagnostic data feed. As is shown in operation 510, an apparatus may include means, such as the data analysis system 104, the processor 303, or the like, for generating a history of operator texts for the primary data feed. As is shown in operation 512, an apparatus may include means, such as the data analysis system 104, the processor 303, or the like, for traversing, using one or more features in the primary data feed or the at least one confirmatory data feed, a decision tree, wherein the decision tree is operable to determine that at least a portion of an operator text is to be generated in an instance in which a feature evaluates as true for at least one node of the decision tree.

FIG. 6 is a flow chart illustrating an example method for generating the operator text using an exemplary natural language generation system. As is shown in operation 602, an apparatus may include means, such as the natural language generation system 106, the processor 303, or the like, for instantiating one or more messages. As is shown in operation 604, an apparatus may include means, such as the natural language generation system 106, the processor 303, or the like, for arranging one or more messages in a document plan data structure in an order in which they are to be linguistically described in the operator text. As is shown in operation 606, an apparatus may include means, such as the natural language generation system 106, the processor 303, or the like, for converting at least one of the one or more messages into a text specification data structure that represents one or more data structures that are representative of a syntactic structure of a sentence As is shown in operation 608, an apparatus may include means, such as the natural language generation system 106, the processor 303, or the like, for applying a grammar to the text specification data structure to generate the operator text.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for
    determining whether an operator text is to be generated in response to a received alert condition by performing data analysis operations, the method comprising:
    analyzing, using a processor, a primary data feed and at least one confirmatory data feed to identify one or more features related to the received alert condition;
    determining whether the received alert condition in the primary data feed is confirmed by at least one confirmatory data feed, wherein the alert condition is validated in an instance in which a signal correlation between the primary data feed and the confirmatory data feed satisfies a correlation threshold;
    determining whether the one or more features in the primary data feed are explainable by at least one diagnostic data feed; and
    traversing, using the one or more features, a decision tree, wherein the decision tree is operable to determine that at least a portion of an operator text is to be generated in an instance in which a feature of the one or more features evaluates as true for at least one node of the decision tree; and
    generating an output text that is displayable in a user interface that describes at least a diagnosis based on the at least one diagnostic data feed for the feature of the one or more features that evaluated as true.

2. The method of claim 1, the data analysis operations further comprising:
    determining that the alert condition is present, wherein the alert condition is at least one of
    received from an alert monitoring system over a data communication link; or
    determined based on a violation of a predetermined constraint by the one or more features in the primary data feed.

3. The method according to claim 1, wherein the one or more features is at least one of a trend, spike, oscillation or step in a data feed.

4. The method according to claim 1, the data analysis operations comprising validating the alert condition by performing validating operations further comprising:
    determining whether an alert condition in the primary data feed is to be discarded based on at least one explanatory data feed, wherein the alert condition is discarded in an instance in which a signal correlation between the primary data feed and the explanatory data feed satisfies a discard threshold.

5. The method according to claim 1, wherein the at least one confirmatory data feed, an at least one explanatory data feed and an at least one diagnostic feed are identified as related to the primary data feed based on a loaded hierarchy.

6. The method according to claim 1, the data analysis operations further comprising:
    determining a time until equipment failure based on the primary data feed; and
    generating an output text that describes the time until equipment failure.

7. The method according to claim 1, further comprising:
    determining an intended recipient of the operator text;
    outputting the operator text in an instance in which the intended recipient is an operator; and outputting a situational analysis text in an instance in which the intended recipient is not an operator.

8. The method according to claim 1, the data analysis operations further comprising:
analyzing the primary data feed and at least one of the confirmatory data feeds to determine whether the primary data feed and the at least one of the confirmatory data feeds is correlated for the one or more features by:
generating a signal correlation coefficient for each of the at least one of the confirmatory data feeds, the coefficient comparing the primary data feed with the at least confirmatory data feed; and
selecting the one or more of the at least one of the confirmatory data feeds in an instance in which a correlation threshold is satisfied; and
accessing a fault table, the fault table describing an associated fault for the feature of the primary data feed.

9. The method according to claim 1, wherein the message data structures comprise numerical data that describes at least one of the alert condition, a description of a stable period for the primary data feed, a description of a behavior of one or more related data feeds or a recommendation.

10. The method according to claim 1, data analysis operations further comprising:
determining an alert condition history over a predetermined time period for a machine that is monitored by the primary data feed; and
causing the operator text to comprise at least a portion of the alert condition history and an indication of the predetermined time period.

11. An apparatus for determining whether an operator text is to be generated in response to a received alert condition, the apparatus comprising:
at least one processor; and
at least one memory including computer program code, the at least one memory and the computer program code configured to, with the at least one processor, cause the apparatus to at least:
analyze a primary data feed and at least one confirmatory data feed to identify one or more features related to the received alert condition;
determine whether the received alert condition in the primary data feed is confirmed by at least one confirmatory data feed, wherein the alert condition is validated in an instance in which a signal correlation between the primary data feed and the confirmatory data feed satisfies a correlation threshold;
determine whether the one or more features in the primary data feed are explainable by at least one diagnostic data feed; and
traverse, using the one or more features, a decision tree, wherein the decision tree is operable to determine that at least a portion of an operator text is to be generated in an instance in which a feature of the one or more features evaluates as true for at least one node of the decision tree; and
generate an output text that is displayable in a user interface that describes at least a diagnosis based on the at least one diagnostic data feed for the feature of the one or more features that evaluated as true.

12. The apparatus of claim 11, wherein the at least one memory including the computer program code is further configured to, with the at least one processor, cause the apparatus to:
determine that the alert condition is present, wherein the alert condition is at least one of
received from an alert monitoring system over a data communication link; or
determined based on a violation of a predetermined constraint by the one or more features of the primary data feed.

13. The apparatus according to claim 11, wherein the one or more features is at least one of a trend, spike, oscillation or step in a data feed.

14. The apparatus according to claim 11, wherein the at least one memory including the computer program code is further configured to, with the at least one processor, cause the apparatus to:
determine whether an alert condition in the primary data feed is to be discarded based on at least one explanatory data feed, wherein the alert condition is discarded in an instance in which a signal correlation between the primary data feed and the explanatory data feed satisfies a discard threshold.

15. The apparatus according to claim 11, wherein the at least one confirmatory data feed, an at least one explanatory data feed and an at least one diagnostic feed are identified as related to the primary data feed based on a loaded hierarchy.

16. The apparatus according to claim 11, wherein the at least one memory including the computer program code is further configured to, with the at least one processor, cause the apparatus to:
determine a time until equipment failure based on the primary data feed; and
generate an output text that describes the time until equipment failure.

17. The apparatus according to claim 11, wherein the at least one memory including the computer program code is further configured to, with the at least one processor, cause the apparatus to:
determine an intended recipient of the operator text;
output the operator text in an instance in which the intended recipient is an operator; and
output a situational analysis text in an instance in which the intended recipient is not an operator.

18. The apparatus according to claim 11, wherein the at least one memory including the computer program code is further configured to, with the at least one processor, cause the apparatus to:
analyze the primary data feed and at least one of the confirmatory data feeds to determine whether the primary data feed and the at least one of the confirmatory data feeds is correlated for the one or more features by:
generating a signal correlation coefficient for each of the at least one of the confirmatory data feeds, the coefficient comparing the primary data feed with the at least confirmatory data feed; and
selecting the one or more of the at least one of the confirmatory data feeds in an instance in which a correlation threshold is satisfied; and
accessing a fault table, the fault table describing an associated fault for the one or more features of the primary data feed.

19. The apparatus according to claim 11, wherein the message data structures comprise numerical data that describes at least one of the alert condition, a description of a stable period for the primary data feed, a description of a behavior of one or more related data feeds or a recommendation.

20. The apparatus according to claim 11, wherein the at least one memory including the computer program code is further configured to, with the at least one processor, cause the apparatus to:

determine an alert condition history over a predetermined time period for a machine that is monitored by the primary data feed; and cause the operator text to comprise at least a portion of the alert condition history and an indication of the predetermined time period.

21. A computer program product for determining whether an operator text is to be generated in response to a received alert condition, the computer program product comprising at least one computer readable non-transitory memory medium having program code instructions stored thereon, the program code instructions which when executed by an apparatus cause the apparatus at least to:

analyze a primary data feed and at least one confirmatory data feed to identify one or more features related to the received alert condition;

determine whether the received alert condition in the primary data feed is confirmed by at least one confirmatory data feed, wherein the alert condition is validated in an instance in which a signal correlation between the primary data feed and the confirmatory data feed satisfies a correlation threshold;

determine whether the one or more features in the primary data feed is explainable by at least one diagnostic data feed; and traverse, using the one or more features, a decision tree, wherein the decision tree is operable to determine that at least a portion of an operator text is to be generated in an instance in which a feature of the one or more features evaluates as true for at least one node of the decision tree; and generate an output text that is displayable in a user interface that describes at least a diagnosis based on the at least one diagnostic data feed for the feature of the one or more features that evaluated as true.

* * * * *